(12) United States Patent
Onishi et al.

(10) Patent No.: US 12,338,454 B2
(45) Date of Patent: Jun. 24, 2025

(54) HELPER PLASMID FOR TRANSFORMATION, METHOD FOR PRODUCING TRANSFORMANT USING THE SAME, AND TRANSFORMATION METHOD

(71) Applicant: TOYOTA JIDOSHA KABUSHIKI KAISHA, Toyota (JP)

(72) Inventors: Toru Onishi, Toyota (JP); Nobuki Tada, Nisshin (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 501 days.

(21) Appl. No.: 16/909,499

(22) Filed: Jun. 23, 2020

(65) Prior Publication Data

US 2020/0399659 A1 Dec. 24, 2020

(30) Foreign Application Priority Data

Jun. 24, 2019 (JP) ................. 2019-116358

(51) Int. Cl.
| | |
|---|---|
| *C12N 15/90* | (2006.01) |
| *C12N 15/00* | (2006.01) |
| *C12N 15/65* | (2006.01) |
| *C12N 15/81* | (2006.01) |

(52) U.S. Cl.
CPC ........... *C12N 15/905* (2013.01); *C12N 15/00* (2013.01); *C12N 15/65* (2013.01); *C12N 15/81* (2013.01); *C12N 2800/80* (2013.01)

(58) Field of Classification Search
CPC ...... C12N 15/905; C12N 15/00; C12N 15/65; C12N 15/81
See application file for complete search history.

(56) References Cited

U.S. PATENT DOCUMENTS

| | | |
|---|---|---|
| 9,476,065 B2 | 10/2016 | Horwitz et al. |
| 2002/0151058 A1 | 10/2002 | Perkins et al. |
| 2012/0202251 A1 | 8/2012 | Cornish et al. |

(Continued)

FOREIGN PATENT DOCUMENTS

| | | |
|---|---|---|
| CN | 106029886 A | 10/2016 |
| JP | 2016533719 A * | 11/2016 |
| WO | 2015/052344 A1 | 4/2015 |

OTHER PUBLICATIONS

Sharan, Shyam K., et al. "Recombineering: a homologous recombination-based method of genetic engineering." Nature protocols 4.2 (2009): 206-223 (Year: 2009).*

(Continued)

*Primary Examiner* — Ram R Shukla
*Assistant Examiner* — Shabana S Meyering
(74) *Attorney, Agent, or Firm* — Sughrue Mion, PLLC

(57) ABSTRACT

A stable transformant, in which a gene of interest is incorporated into the genome, is simply and efficiently produced. A method for producing a transformant, comprising a step of introducing into a host, linear genome-introduced nucleic acid fragment(s) comprising a gene of interest and a helper plasmid for transformation having a pair of homologous recombination sequences for incorporation of the linear genome-introduced nucleic acid fragment(s), and then selecting a transformant, in which the gene of interest is incorporated into the predetermined position in the host genome and the gene of interest is expressed therein.

8 Claims, 10 Drawing Sheets

Specification includes a Sequence Listing.

(56) References Cited

U.S. PATENT DOCUMENTS

| | | | |
|---|---|---|---|
| 2015/0184199 A1* | 7/2015 | Horwitz | C12Q 1/6897 |
| | | | 435/254.11 |
| 2016/0017344 A1 | 1/2016 | Boeke et al. | |
| 2016/0046972 A1* | 2/2016 | Boeke | C12N 15/66 |
| | | | 435/254.2 |
| 2018/0326093 A1* | 11/2018 | Clube | C12P 19/34 |
| 2022/0186196 A1 | 6/2022 | Wacker et al. | |

OTHER PUBLICATIONS

Joska, Tammy M., et al. "A universal cloning method based on yeast homologous recombination that is simple, efficient, and versatile." Journal of microbiological methods 100 (2014): 46-51 (Year: 2014).*

JP 2016533719 A, English translation (see OA Appendix) (Year: 2016).*

Mizutani, Kimihiko. "High-throughput plasmid construction using homologous recombination in yeast: its mechanisms and application to protein production for X-ray crystallography." Bioscience, Biotechnology, and Biochemistry 79.1 (2015): 1-10 (Year: 2015).*

Siegl, Theresa, et al. "I-Sce I endonuclease: a new tool for DNA repair studies and genetic manipulations in streptomycetes." Applied microbiology and biotechnology 87 (2010): 1525-1532 (Year: 2010).*

Nagano, Yukio, et al. "Yeast-based recombineering of DNA fragments into plant transformation vectors by one-step transformation." Plant cell reports 26 (2007): 2111-2117 (Year: 2007).*

Mizutani K. High-throughput plasmid construction using homologous recombination in yeast: its mechanisms and application to protein production for X-ray crystallography. Biosci Biotechnol Biochem. 2015;79(1):1-10. (Year: 2015).*

Kunes et al., J Mol Biol. Aug. 5, 1985;184(3):375-87. (Year: 1985).*

Gietz, R.D., et al. "High-efficiency yeast transformation using the LiAc/SS carrier DNA/PEG method" Nature Protocols, 2007, pp. 31-34, vol. 2 No. 1.

Storici, F. et al. "Chromosomal site-specific double-strand breaks are efficiently targeted for repair by oligonucleotides in yeast.", PNAS, 2003, pp. 14994-14999, vol. 100, No. 25.

Dicarlo J.E., et al. "Genome engineering in *Saccharomyces cerevisiae* using CRISPR-Cas systems." Nucleic Acids Research, 2013, pp. 4336-4343, vol. 41, No. 7.

Nagano et al., "DNA cloning by homologous recombination", Seibutsu-kogaku kaishi, 2015, vol. 93, No. 10, pp. 623 to 626 (10 pages total).

Iizasa et al., "Highly efficient yeast-based in vivo DNA cloning of multiple DNA fragments and the simultaneous construction of yeast/*Escherichia coli* shuttle vectors", BioTechniques, 2006, vol. 40, No. 1, pp. 79-83 (5 pages total).

Nagano et al., "DNA cloning by homologous recombination", Biotechnology, 2015, vol. 93, No. 10, pp. 623-626 (10 pages total).

Iizasa et al., "Highly efficient yeast-based in vivo DNA cloning of multiple DNA fragments and the simultaneous construction of yeast/*Escherichia coli* shuttle vectors", BioTechniques, Jan. 2006, vol. 40, No. 1, pp. 79-83 (5 pages total).

* cited by examiner

SEQUENCE LISTING

<160> NUMBER OF SEQ ID NOS: 52

<210> SEQ ID NO 1
<211> LENGTH: 796
<212> TYPE: DNA
<213> ORGANISM: Saccharomyces cerevisiae

<400> SEQUENCE: 1

```
agcatgtata acaaacactg attttgttt tgagttttaa aagatatcca tttactaaca      60
ttcgaggtgt acaagcacaa gttttgcagt gaaaaacatt aagaaaaacc aagttatgaa     120
tttgggtcca aacagtaagt tattgaaaga atacaagtca caattgatag aattaaatat    180
agaacaattt gaagccggta tcggtttgat tttaggtgac gcttatatta gatccagaga    240
cgaaggtaaa acttactgta tgcaattcga atggaaaaac aaggcatata tggatcatgt    300
atgcttgtta tacgaccaat gggtcttgtc accacctcat aaaaaggaaa gagtcaatca    360
cttgggtaac ttagttatta cctggggtgc ccaaactttt aagcaccaag cttttaataa    420
gttggcaaat ttgtttattg ttaacaacaa aaagacaatc ccaaacaact tggtagaaaa    480
ctatttgacc cctatgtctt tggcttactg gttcatggat gacggtggta aatgggatta    540
caataagaac tccacaaata agagtatcgt tttgaacact caatctttta ctttcgaaga    600
agttgaatac ttggtaaagg gtttgagaaa taagttccaa ttgaactgtt acgttaaaat    660
taataagaac aagccaatta tatacattga ttctatgtca tatttgatat tctacaattt    720
gatcaaacct tatttgattc cacaaatgat gtataagtta ccaaacacta tctcctccga    780
aaccttcttg aaatga                                                   796
```

<210> SEQ ID NO 2
<211> LENGTH: 235
<212> TYPE: PRT
<213> ORGANISM: Saccharomyces cerevisiae

<400> SEQUENCE: 2

Met Lys Asn Ile Lys Lys Asn Gln Val Met Asn Leu Gly Pro Asn Ser
1               5                   10                  15

Lys Leu Leu Lys Glu Tyr Lys Ser Gln Leu Ile Glu Leu Asn Ile Glu
                20                  25                  30

Gln Phe Glu Ala Gly Ile Gly Leu Ile Leu Gly Asp Ala Tyr Ile Arg
            35                  40                  45

Ser Arg Asp Glu Gly Lys Thr Tyr Cys Met Gln Phe Glu Trp Lys Asn
        50                  55                  60

Lys Ala Tyr Met Asp His Val Cys Leu Leu Tyr Asp Gln Trp Val Leu
65                  70                  75                  80

Ser Pro Pro His Lys Lys Glu Arg Val Asn His Leu Gly Asn Leu Val
                85                  90                  95

Ile Thr Trp Gly Ala Gln Thr Phe Lys His Gln Ala Phe Asn Lys Leu
            100                 105                 110

Ala Asn Leu Phe Ile Val Asn Asn Lys Lys Thr Ile Pro Asn Asn Leu
        115                 120                 125

Val Glu Asn Tyr Leu Thr Pro Met Ser Leu Ala Tyr Trp Phe Met Asp
    130                 135                 140

```
Asp Gly Gly Lys Trp Asp Tyr Asn Lys Asn Ser Thr Asn Lys Ser Ile
145                 150                 155                 160

Val Leu Asn Thr Gln Ser Phe Thr Phe Glu Glu Val Glu Tyr Leu Val
            165                 170                 175

Lys Gly Leu Arg Asn Lys Phe Gln Leu Asn Cys Tyr Val Lys Ile Asn
        180                 185                 190

Lys Asn Lys Pro Ile Ile Tyr Ile Asp Ser Met Ser Tyr Leu Ile Phe
    195                 200                 205

Tyr Asn Leu Ile Lys Pro Tyr Leu Ile Pro Gln Met Met Tyr Lys Leu
210                 215                 220

Pro Asn Thr Ile Ser Ser Glu Thr Phe Leu Lys
225                 230                 235

<210> SEQ ID NO 3
<211> LENGTH: 20
<212> TYPE: DNA
<213> ORGANISM: Artificial
<220> FEATURE:
<223> OTHER INFORMATION: Synthetic DNA

<400> SEQUENCE: 3
acggattaga agccgccgag                                              20

<210> SEQ ID NO 4
<211> LENGTH: 29
<212> TYPE: DNA
<213> ORGANISM: Artificial
<220> FEATURE:
<223> OTHER INFORMATION: Synthetic DNA

<400> SEQUENCE: 4 ggtttttct ccttgacgtt aaagtatag                                     29

<210> SEQ ID NO 5
<211> LENGTH: 48
<212> TYPE: DNA
<213> ORGANISM: Artificial
<220> FEATURE:
<223> OTHER INFORMATION: Synthetic DNA

<400> SEQUENCE: 5
tcaaggagaa aaaccagca tgtataacaa acactgattt ttgttttg                48

<210> SEQ ID NO 6
<211> LENGTH: 38
<212> TYPE: DNA
<213> ORGANISM: Artificial
<220> FEATURE:
<223> OTHER INFORMATION: Synthetic DNA

<400> SEQUENCE: 6
tcttaatgtt tttcactgca aaacttgtgc ttgtacac                          38

<210> SEQ ID NO 7
<211> LENGTH: 29
<212> TYPE: DNA
<213> ORGANISM: Artificial
<220> FEATURE:
<223> OTHER INFORMATION: Synthetic DNA

<400> SEQUENCE: 7
tgaaaaacat taagaaaaac caagttatg                                    29
```

<210> SEQ ID NO 8
<211> LENGTH: 37
<212> TYPE: DNA
<213> ORGANISM: Artificial
<220> FEATURE:
<223> OTHER INFORMATION: Synthetic DNA

<400> SEQUENCE: 8
gcgtgacata actaatcatt tcaagaaggt ttcggag                        37

<210> SEQ ID NO 9
<211> LENGTH: 26
<212> TYPE: DNA
<213> ORGANISM: Artificial
<220> FEATURE:
<223> OTHER INFORMATION: Synthetic DNA

<400> SEQUENCE: 9
ttagttatgt cacgcttaca ttcacg                                   26

<210> SEQ ID NO 10
<211> LENGTH: 59
<212> TYPE: DNA
<213> ORGANISM: Artificial
<220> FEATURE:
<223> OTHER INFORMATION: Synthetic DNA

<400> SEQUENCE: 10
aattgcccga ctcatattac cctgttatcc ctaagcttgc aaattaaagc cttcgagcg     59

<210> SEQ ID NO 11
<211> LENGTH: 18
<212> TYPE: DNA
<213> ORGANISM: Artificial
<220> FEATURE:
<223> OTHER INFORMATION: Synthetic DNA

<400> SEQUENCE: 11
atgagtcggg caattccg                                            18

<210> SEQ ID NO 12
<211> LENGTH: 46
<212> TYPE: DNA
<213> ORGANISM: Artificial
<220> FEATURE:
<223> OTHER INFORMATION: Synthetic DNA

<400> SEQUENCE: 12
ctgggcctcc atgtctatcg ttaatatttc gtatgtgtat tctttg             46

<210> SEQ ID NO 13
<211> LENGTH: 20
<212> TYPE: DNA
<213> ORGANISM: Artificial
<220> FEATURE:
<223> OTHER INFORMATION: Synthetic DNA

<400> SEQUENCE: 13
gacatggagg cccagaatac                                          20

<210> SEQ ID NO 14
<211> LENGTH: 24
<212> TYPE: DNA
<213> ORGANISM: Artificial
<220> FEATURE:
<223> OTHER INFORMATION: Synthetic DNA
<210> SEQ ID NO 15
<211> LENGTH: 41
<212> TYPE: DNA
<213> ORGANISM: Artificial
<220> FEATURE:
<223> OTHER INFORMATION: Synthetic DNA

<400> SEQUENCE: 15
cgaacataaa caaccatggg taaggaaaag actcacgttt c        41

<210> SEQ ID NO 16
<211> LENGTH: 46
<212> TYPE: DNA
<213> ORGANISM: Artificial
<220> FEATURE:
<223> OTHER INFORMATION: Synthetic DNA

<400> SEQUENCE: 16
tattgtcagt actgattaga aaaactcatc gagcatcaaa tgaaac    46

<210> SEQ ID NO 17
<211> LENGTH: 35
<212> TYPE: DNA
<213> ORGANISM: Artificial
<220> FEATURE:
<223> OTHER INFORMATION: Synthetic DNA

<400> SEQUENCE: 17
tcagtactga caataaaaag attcttgttt tcaag                35

<210> SEQ ID NO 18
<211> LENGTH: 27
<212> TYPE: DNA
<213> ORGANISM: Artificial
<220> FEATURE:
<223> OTHER INFORMATION: Synthetic DNA

<400> SEQUENCE: 18
cagtatagcg accagcattc acatacg                        27

<210> SEQ ID NO 19
<211> LENGTH: 48
<212> TYPE: DNA
<213> ORGANISM: Artificial
<220> FEATURE:
<223> OTHER INFORMATION: Synthetic DNA

<400> SEQUENCE: 19
atagcataca ttatacgaag ttatcccaca caccatagct tcaaaatg  48

<210> SEQ ID NO 20
<211> LENGTH: 37
<212> TYPE: DNA
<213> ORGANISM: Artificial
<220> FEATURE:
<223> OTHER INFORMATION: Synthetic DNA

<400> SEQUENCE: 20
caccgaaatc ttcatcccct tagattagatt gctatgc            37

<210> SEQ ID NO 21

<211> LENGTH: 41
<212> TYPE: DNA
<213> ORGANISM: Artificial
<220> FEATURE:
<223> OTHER INFORMATION: Synthetic DNA

<400> SEQUENCE: 21
gctggtcgct atactgcgtg atttacatat actacaagtc g          41

<210> SEQ ID NO 22
<211> LENGTH: 48
<212> TYPE: DNA
<213> ORGANISM: Artificial
<220> FEATURE:
<223> OTHER INFORMATION: Synthetic DNA

<400> SEQUENCE: 22
aaaaacataa gacaaattac cctgttatcc ctatgaccgg atgaaacc    48

<210> SEQ ID NO 23
<211> LENGTH: 37
<212> TYPE: DNA
<213> ORGANISM: Artificial
<220> FEATURE:
<223> OTHER INFORMATION: Synthetic DNA

<400> SEQUENCE: 23
gggataacag ggtaatggta cccaattcgc cctatag               37

<210> SEQ ID NO 24
<211> LENGTH: 20
<212> TYPE: DNA
<213> ORGANISM: Artificial
<220> FEATURE:
<223> OTHER INFORMATION: Synthetic DNA

<400> SEQUENCE: 24
taccgcacag atgcgtaagg                                  20

<210> SEQ ID NO 25
<211> LENGTH: 44
<212> TYPE: DNA
<213> ORGANISM: Artificial
<220> FEATURE:
<223> OTHER INFORMATION: Synthetic DNA

<400> SEQUENCE: 25
ttacgcatct gtgcggtaag gaatcatagt ttcatgattt tctg       44

<210> SEQ ID NO 26
<211> LENGTH: 45
<212> TYPE: DNA
<213> ORGANISM: Artificial
<220> FEATURE:
<223> OTHER INFORMATION: Synthetic DNA

<400> SEQUENCE: 26
caggatgacg cctaaaaaga ttctcttttt ttatgatatt tgtac      45

<210> SEQ ID NO 27
<211> LENGTH: 20
<212> TYPE: DNA
<213> ORGANISM: Artificial
<220> FEATURE:
<223> OTHER INFORMATION: Synthetic DNA

<400> SEQUENCE: 27
ttaggcgtca tcctgtgctc                                               20

<210> SEQ ID NO 28
<211> LENGTH: 35
<212> TYPE: DNA
<213> ORGANISM: Artificial
<220> FEATURE:
<223> OTHER INFORMATION: Synthetic DNA

<400> SEQUENCE: 28
cacactaaat taataatgaa gatttcggtg atccc                              35

<210> SEQ ID NO 29
<211> LENGTH: 33
<212> TYPE: DNA
<213> ORGANISM: Artificial
<220> FEATURE:
<223> OTHER INFORMATION: Synthetic DNA

<400> SEQUENCE: 29
tattaattta gtgtgtgtat ttgtgtttgt gtg                                33

<210> SEQ ID NO 30
<211> LENGTH: 40
<212> TYPE: DNA
<213> ORGANISM: Artificial
<220> FEATURE:
<223> OTHER INFORMATION: Synthetic DNA

<400> SEQUENCE: 30
gcagattgta ctgagagtac gacatcgtcg aatatgattc                         40

<210> SEQ ID NO 31
<211> LENGTH: 26
<212> TYPE: DNA
<213> ORGANISM: Artificial
<220> FEATURE:
<223> OTHER INFORMATION: Synthetic DNA

<400> SEQUENCE: 31
actctcagta caatctgctc tgatgc                                        26

<210> SEQ ID NO 32
<211> LENGTH: 38
<212> TYPE: DNA
<213> ORGANISM: Artificial
<220> FEATURE:
<223> OTHER INFORMATION: Synthetic DNA

<400> SEQUENCE: 32
cggcttctaa tccgtgctcc agcttttgtt ccctttag                           38

<210> SEQ ID NO 33
<211> LENGTH: 48
<212> TYPE: DNA
<213> ORGANISM: Artificial
<220> FEATURE:
<223> OTHER INFORMATION: Synthetic DNA

<400> SEQUENCE: 33
tcaaggagaa aaaccagca tgtataacaa acactgattt tgttttg                  48

<210> SEQ ID NO 34

<211> LENGTH: 38
<212> TYPE: DNA
<213> ORGANISM: Artificial
<220> FEATURE:
<223> OTHER INFORMATION: Synthetic DNA

<400> SEQUENCE: 34
cggcttctaa tccgtgctcc agcttttgtt ccctttag                38

<210> SEQ ID NO 35
<211> LENGTH: 20
<212> TYPE: DNA
<213> ORGANISM: Artificial
<220> FEATURE:
<223> OTHER INFORMATION: Synthetic DNA

<400> SEQUENCE: 35
acggattaga agccgccgag                20

<210> SEQ ID NO 36
<211> LENGTH: 29
<212> TYPE: DNA
<213> ORGANISM: Artificial
<220> FEATURE:
<223> OTHER INFORMATION: Synthetic DNA

<400> SEQUENCE: 36
ggttttttct ccttgacgtt aaagtatag                29

<210> SEQ ID NO 37
<211> LENGTH: 26
<212> TYPE: DNA
<213> ORGANISM: Artificial
<220> FEATURE:
<223> OTHER INFORMATION: Synthetic DNA

<400> SEQUENCE: 37
ttatcgatga taagctgtca aagatg                26

<210> SEQ ID NO 38
<211> LENGTH: 30
<212> TYPE: DNA
<213> ORGANISM: Artificial
<220> FEATURE:
<223> OTHER INFORMATION: Synthetic DNA

<400> SEQUENCE: 38 tggtttttc tccttgacgt taaagtatag                30

<210> SEQ ID NO 39
<211> LENGTH: 26
<212> TYPE: DNA
<213> ORGANISM: Artificial
<220> FEATURE:
<223> OTHER INFORMATION: Synthetic DNA

<400> SEQUENCE: 39
ttatcgatga taagctgtca aagatg                26

<210> SEQ ID NO 40
<211> LENGTH: 45
<212> TYPE: DNA
<213> ORGANISM: Artificial
<220> FEATURE:
<223> OTHER INFORMATION: Synthetic DNA

```
<400> SEQUENCE: 40
tcggttagag cggatgtggg gggagggcgt gaatgtaagc gtgac           45

<210> SEQ ID NO 41
<211> LENGTH: 20
<212> TYPE: DNA
<213> ORGANISM: Artificial
<220> FEATURE:
<223> OTHER INFORMATION: Synthetic DNA

<400> SEQUENCE: 41
atccgctcta accgaaaagg                                       20

<210> SEQ ID NO 42
<211> LENGTH: 22
<212> TYPE: DNA
<213> ORGANISM: Artificial
<220> FEATURE:
<223> OTHER INFORMATION: Synthetic DNA

<400> SEQUENCE: 42
agcttgcaaa ttaaagcctt cg                                    22

<210> SEQ ID NO 43
<211> LENGTH: 58
<212> TYPE: DNA
<213> ORGANISM: Artificial
<220> FEATURE:
<223> OTHER INFORMATION: Synthetic DNA

<400> SEQUENCE: 43
tttaatttgc aagcttttcc acttattcaa cctttaatg agtcgggcaa ttccgaag    58

<210> SEQ ID NO 44
<211> LENGTH: 57
<212> TYPE: DNA
<213> ORGANISM: Artificial
<220> FEATURE:
<223> OTHER INFORMATION: Synthetic DNA

<400> SEQUENCE: 44
gcttatcatc gataataaaa ggttgaataa gtggaaatga ccggatgaaa ccaccgg    57

<210> SEQ ID NO 45
<211> LENGTH: 20
<212> TYPE: DNA
<213> ORGANISM: Artificial
<220> FEATURE:
<223> OTHER INFORMATION: Synthetic DNA

<400> SEQUENCE: 45
acggattaga agccgccgag                                       20

<210> SEQ ID NO 46
<211> LENGTH: 18
<212> TYPE: DNA
<213> ORGANISM: Artificial
<220> FEATURE:
<223> OTHER INFORMATION: Synthetic DNA

<400> SEQUENCE: 46
tcatgcccct gagctgcg                                         18

<210> SEQ ID NO 47
```

```
<211> LENGTH: 20
<212> TYPE: DNA
<213> ORGANISM: Artificial
<220> FEATURE:
<223> OTHER INFORMATION: Synthetic DNA

<400> SEQUENCE: 47
gacatggagg cccagaatac                                              20

<210> SEQ ID NO 48
<211> LENGTH: 27
<212> TYPE: DNA
<213> ORGANISM: Artificial
<220> FEATURE:
<223> OTHER INFORMATION: Synthetic DNA

<400> SEQUENCE: 48
cagtatagcg accagcattc acatacg                                      27

<210> SEQ ID NO 49
<211> LENGTH: 26
<212> TYPE: DNA
<213> ORGANISM: Artificial
<220> FEATURE:
<223> OTHER INFORMATION: Synthetic DNA

<400> SEQUENCE: 49
ttaagtgcgc agaaagtaat atcatg                                       26

<210> SEQ ID NO 50
<211> LENGTH: 18
<212> TYPE: DNA
<213> ORGANISM: Artificial
<220> FEATURE:
<223> OTHER INFORMATION: Synthetic DNA

<400> SEQUENCE: 50
tgaccggatg aaaccacc                                                18

<210> SEQ ID NO 51
<211> LENGTH: 23
<212> TYPE: DNA
<213> ORGANISM: Artificial
<220> FEATURE:
<223> OTHER INFORMATION: Synthetic DNA

<400> SEQUENCE: 51
ggtttcagat cacgatggat aac                                          23

<210> SEQ ID NO 52
<211> LENGTH: 21
<212> TYPE: DNA
<213> ORGANISM: Artificial
<220> FEATURE:
<223> OTHER INFORMATION: Synthetic DNA

<400> SEQUENCE: 52
gcaacagtaa aagggatcag c                                            21
```

HELPER PLASMID FOR TRANSFORMATION, METHOD FOR PRODUCING TRANSFORMANT USING THE SAME, AND TRANSFORMATION METHOD

CROSS REFERENCE TO RELATED APPLICATIONS

The present application claims priority from Japanese patent application JP 2019-116358 filed on Jun. 24, 2019, the content of which is hereby incorporated by reference into this application.

INCORPORATION BY REFERENCE OF SEQUENCE LISTING

The instant application contains a Sequence Listing which has been filed electronically in txt format and is hereby incorporated by reference in its entirety. Said txt copy, created on Jun. 23, 2020, is named Q256128_Sequnce_Listing_as_filed and is 12,418 bytes in size.

BACKGROUND

Technical Field

The present disclosure relates to a helper plasmid for transformation that is used upon introduction of a gene of interest into a host, a method for producing a transformant using the helper plasmid for transformation, and a transformation method using the helper plasmid for transformation.

Background Art

In general, a technique of introducing a gene of interest into a host cell from the outside is referred to as transformation or gene recombination, and a cell into which the gene of interest is introduced is referred to as a transformant or a recombinant. By efficiently producing such a transformant utilizing a transformation technique, acceleration and/or efficiency of microbial metabolic engineering can be promoted, for example, utilizing a synthetic biological technique. Herein, the synthetic biological technique means a technique of promptly turning a cycle consisting of the designing, construction and learning of a production host. Among others, in synthetic biology of using a yeast as a host, it is important to efficiently construct a host, namely, to efficiently produce a recombinant yeast.

Transformation using a yeast as a host is broadly classified into a method of using a circular plasmid into which a gene of interest is incorporated, and a method of using a linear vector comprising a gene of interest. It is easy to introduce a gene of interest into a yeast using a circular plasmid, and a transformed yeast can be produced at a high efficiency of approximately $10^{-2}$ (Gietz, R. D., et al. "High-efficiency yeast transformation using the LiAc/SS carrier DNA/PEG method." Nature Protocols. 2 (2007): 31-34.). On the other hand, when a gene of interest is introduced into a yeast using a linear vector, it is necessary to incorporate the gene of interest into the genome according to homologous recombination. Thus, a transformed yeast can be produced only at an efficiency of approximately $10^{-6}$ (Storici, F, et al. "Chromosomal site-specific double-strand breaks are efficiently targeted for repair by oligonucleotides in yeast." Proc. Natl. Acad. Sci. USA. 100 (2003): 14994-14999.).

As described above, the method of introducing a gene of interest into a yeast using a circular plasmid is highly efficient. However, such a circular plasmid may be detached in some case, and thus, a stable recombinant yeast cannot be produced. On the other hand, in the method of introducing a gene of interest into a yeast using a linear vector, the gene of interest is stably incorporated into the genome. However, as described above, this method is not considered to be highly efficient.

In order to improve the efficiency of introducing a gene of interest into the genome, known is a technique, in which the target sequence of target-specific endonuclease such as homing endonuclease has previously been introduced into a scheduled introduction site in the genome, and then, the double strands at the site have previously been cleaved (Storici, F, et al. "Chromosomal site-specific double-strand breaks are efficiently targeted for repair by oligonucleotides in yeast. "Proc. Natl. Acad. Sci. USA. 100 (2003): 14994-14999.).

Moreover, also known is a technique, in which the double strands of a scheduled introduction site in the genome has previously been cleaved by applying a technique of cleaving any given nucleotide sequence, such as CRISPR-Cas9 or TALEN, instead of the target-specific endonuclease (DiCarlo, J. E., et al. "Genome engineering in *Saccharomyces cerevisiae* using CRISPR-Cas systems." Nucleic Acids Res. 41 (2013): 4336-4343.). Hence, it is possible to improve homologous recombination efficiency to approximately 102 to $10^{-1}$ by previously cleaving the double strands at the site into which a gene of interest is to be introduced.

However, in these methods of improving the efficiency of introducing a gene of interest, it has been necessary to previously introduce a nuclease target sequence into a scheduled introduction site in the genome, or it has been necessary to produce guide RNA or the like to the target site. Thus, these methods of improving the efficiency of introducing a gene of interest are complicated, and require various steps, in addition to production of a DNA fragment for homologous recombination containing a gene of interest and the subsequent transformation using the produced DNA fragment.

In addition, US 2016/0017344 discloses a plasmid comprising a selective marker having an intron configured to sandwich a homing endonuclease target sequence with telomere seed sequences. In the case of the plasmid disclosed in US 2016/0017344, as a result of the expression of the homing endonuclease, the circular plasmid can be converted to linear molecules and can be stably present because of the telomere seed sequence at the terminus.

US 2016/0017344

Gietz, R. D., et al. "High-efficiency yeast transformation using the LiAc/SS carrier DNA/PEG method." Nature Protocols. 2 (2007): 31-34.

Storici, F, et al. "Chromosomal site-specific double-strand breaks are efficiently targeted for repair by oligonucleotides in yeast." Proc. Natl. Acad. Sci. USA. 100 (2003): 14994-14999.

DiCarlo, J. E., et al. "Genome engineering in *Saccharomyces cerevisiae* using CRISPR-Cas systems." Nucleic Acids Res. 41 (2013): 4336-4343.

SUMMARY

However, all of the aforementioned methods have been problematic in that a stable transformant, in which a gene of interest is incorporated into the genome, cannot be simply and efficiently produced according to the methods. Hence, considering the aforementioned circumstances, the present disclosure provides: a method for producing a transformant, wherein the method is capable of simply and efficiently producing a stable transformant, in which a gene of interest is incorporated into the genome; a transformation method; and a helper plasmid for transformation that can be used in these methods.

The present disclosure that achieves the aforementioned exemplary embodiments includes the following.

(1) A method for producing a transformant, comprising steps of:
  introducing into a host, one or a plurality of linear genome-introduced nucleic acid fragments each comprising a gene of interest to be introduced into a predetermined position on a genome, and a helper plasmid for transformation comprising a pair of homologous recombination sequences for incorporation of the linear genome-introduced nucleic acid fragments, wherein, in a state in which the linear genome-introduced nucleic acid fragments are incorporated into the helper plasmid for transformation, a pair of homologous recombination sequences for homologous recombination that takes place outside of the gene of interest and at the predetermined position on the genome, and a pair of endonuclease target sequences outside of the pair of homologous recombination sequences are disposed; and
  selecting a transformant, in which the gene of interest is incorporated into the predetermined position on the host genome and the gene of interest is expressed therein.

(2) The method for producing a transformant according to the above (1), wherein the helper plasmid for transformation comprises a pair of homologous recombination sequences to be homologously recombined with the outside of the gene of interest in the linear genome-introduced nucleic acid fragment and a pair of endonuclease target sequences disposed on the side opposite to the position into which the linear genome-introduced nucleic acid fragment is incorporated via the homologous recombination sequences.

(3) The method for producing a transformant according to the above (1), wherein the linear genome-introduced nucleic acid fragment comprises the pair of homologous recombination sequences to be incorporated into the predetermined position of the genome at positions sandwiching the gene of interest, the pair of endonuclease target sequences outside of the pair of homologous recombination sequences, and the pair of homologous recombination sequences for homologous recombination with the helper plasmid for transformation outside of the pair of endonuclease target sequences.

(4) The method for producing a transformant according to the above (1), wherein the helper plasmid for transformation comprises a target-specific endonuclease gene that specifically cleaves the double strands of the endonuclease target sequences in an expressible state.

(5) The method for producing a transformant according to the above (4), wherein the target-specific endonuclease gene is a homing endonuclease gene.

(6) The method for producing a transformant according to the above (5), wherein the endonuclease target sequence is a sequence specifically recognized by homing endonuclease.

(7) The method for producing a transformant according to the above (4), wherein the helper plasmid for transformation comprises an inducible promoter that regulates the expression of the target-specific endonuclease gene.

(8) The method for producing a transformant according to the above (1), wherein the plurality of linear genome-introduced nucleic acid fragments consist of a first linear genome-introduced nucleic acid fragment to the $n^{th}$ linear genome-introduced nucleic acid fragment (wherein n is an integer of 2 or more), and the 3-terminal side of the $m^{th}$ linear genome-introduced nucleic acid fragment (wherein m is an integer satisfying $1 \leq m \leq n-1$) has a sequence homologously recombined with the 5-terminal side of the $m^{th}+1$ linear genome-introduced nucleic acid fragment.

(9) A transformation method, comprising a step of introducing into a host, one or several types of linear genome-introduced nucleic acid fragments each comprising a gene of interest to be introduced into a predetermined position on a genome, and a helper plasmid for transformation having a pair of homologous recombination sequences for incorporation of the linear genome-introduced nucleic acid fragments, wherein, in a state in which the linear genome-introduced nucleic acid fragments are incorporated into the helper plasmid for transformation, a pair of homologous recombination sequences for homologous recombination that takes place outside of the gene of interest and at the predetermined position on the genome, and a pair of endonuclease target sequences outside of the pair of homologous recombination sequences are disposed,
  wherein the gene of interest is expressed.

(10) The transformation method according to the above (9), wherein the helper plasmid for transformation comprises a pair of homologous recombination sequences to be homologously recombined with the outside of the gene of interest in the linear genome-introduced nucleic acid fragment and a pair of endonuclease target sequences disposed on the side opposite to the position into which the linear genome-introduced nucleic acid fragment is incorporated via the homologous recombination sequences.

(11) The transformation method according to the above (9), wherein the linear genome-introduced nucleic acid fragment comprises the pair of homologous recombination sequences to be incorporated into the predetermined position of the genome at positions sandwiching the gene of interest, the pair of endonuclease target sequences outside of the pair of homologous recombination sequences, and the pair of homologous recombination sequences for homologous recombination with the helper plasmid for transformation outside of the pair of endonuclease target sequences.

(12) The transformation method according to the above (9), wherein the helper plasmid for transformation comprises a target-specific endonuclease gene that specifically cleaves the double strands of the endonuclease target sequences in an expressible state.

(13) The transformation method according to the above (12), wherein the target-specific endonuclease gene is a homing endonuclease gene.

(14) The transformation method according to the above (13), wherein the endonuclease target sequence is a sequence specifically recognized by homing endonuclease.

(15) The transformation method according to the above (12), wherein the helper plasmid for transformation comprises an inducible promoter that regulates the expression of the target-specific endonuclease gene.

(16) The transformation method according to the above (9), wherein the several types of linear genome-introduced nucleic acid fragments consist of a first linear genome-introduced nucleic acid fragment to the $n^{th}$ linear genome-introduced nucleic acid fragment (wherein n is an integer of 2 or more), and the 3-terminal side of the $m^{th}$ linear genome-introduced nucleic acid fragment (wherein m is an integer satisfying $1 \leq m \leq n-1$) has a sequence homologously recombined with the 5-terminal side of the $m^{th}+1$ linear genome-introduced nucleic acid fragment.

(17) A helper plasmid for transformation, which is capable of incorporating into a genome, a linear genome-introduced nucleic acid fragment comprising a gene of interest to be introduced into a predetermined position on the genome, and which comprises a pair of homologous recombination sequences to be homologously recombined with the outside of the gene of interest in the linear genome-introduced nucleic acid fragment, and a pair of endonuclease target sequences disposed on the side opposite to the position into which the linear genome-introduced nucleic acid fragment is incorporated via the homologous recombination sequences.

(18) The helper plasmid for transformation according to the above (17), comprising a target-specific endonuclease gene that specifically cleaves the double strands of the endonuclease target sequences in an expressible state.

(19) The helper plasmid for transformation according to the above (18), wherein the target-specific endonuclease gene is a homing endonuclease gene.

(20) The helper plasmid for transformation according to the above (19), wherein the endonuclease target sequence is a sequence specifically recognized by homing endonuclease.

(21) The helper plasmid for transformation according to the above (18), comprising an inducible promoter regulating the expression of the target-specific endonuclease gene.

In the method for producing a transformant according to the present disclosure, in a state in which a linear genome-introduced nucleic acid fragment(s) comprising a gene of interest are incorporated into a helper plasmid for transformation, the gene of interest is sandwiched with a pair of endonuclease target sequences. Accordingly, a transformant formed by incorporating a gene of interest into a host genome can be efficiently produced.

Furthermore, in the transformation method of the present disclosure, in a state in which a linear genome-introduced nucleic acid fragment(s) comprising a gene of interest are incorporated into a helper plasmid for transformation, the gene of interest is sandwiched with a pair of endonuclease target sequences. Accordingly, excellent transformation efficiency of producing a transformant formed by incorporating a gene of interest into a host genome can be achieved.

By utilizing the helper plasmid for transformation according to the present disclosure, a transformant formed by incorporating a gene of interest into a host genome can be efficiently produced.

DETAILED DESCRIPTION

Hereinafter, the present disclosure will be described in more detail, using drawings and examples.

According to the method for producing a transformant and the transformation method according to the present disclosure (hereinafter collectively referred to as "the present method"), a linear genome-introduced nucleic acid fragment(s) comprising a gene of interest to be incorporated into a host genome, and a helper plasmid for transformation, into which the linear genome-introduced nucleic acid fragment(s) are incorporated according to homologous recombination, are introduced into the host. According to the present method, a linear genome-introduced nucleic acid fragment(s) are incorporated into a helper plasmid for transformation according to homologous recombination. Thereafter, the gene of interest sandwiched with a pair of homologous recombination sequences can be cleaved by predetermined endonuclease in the host, and the gene of interest can be then incorporated into the genome according to homologous recombination occurring with the host genome.

Figure 1:
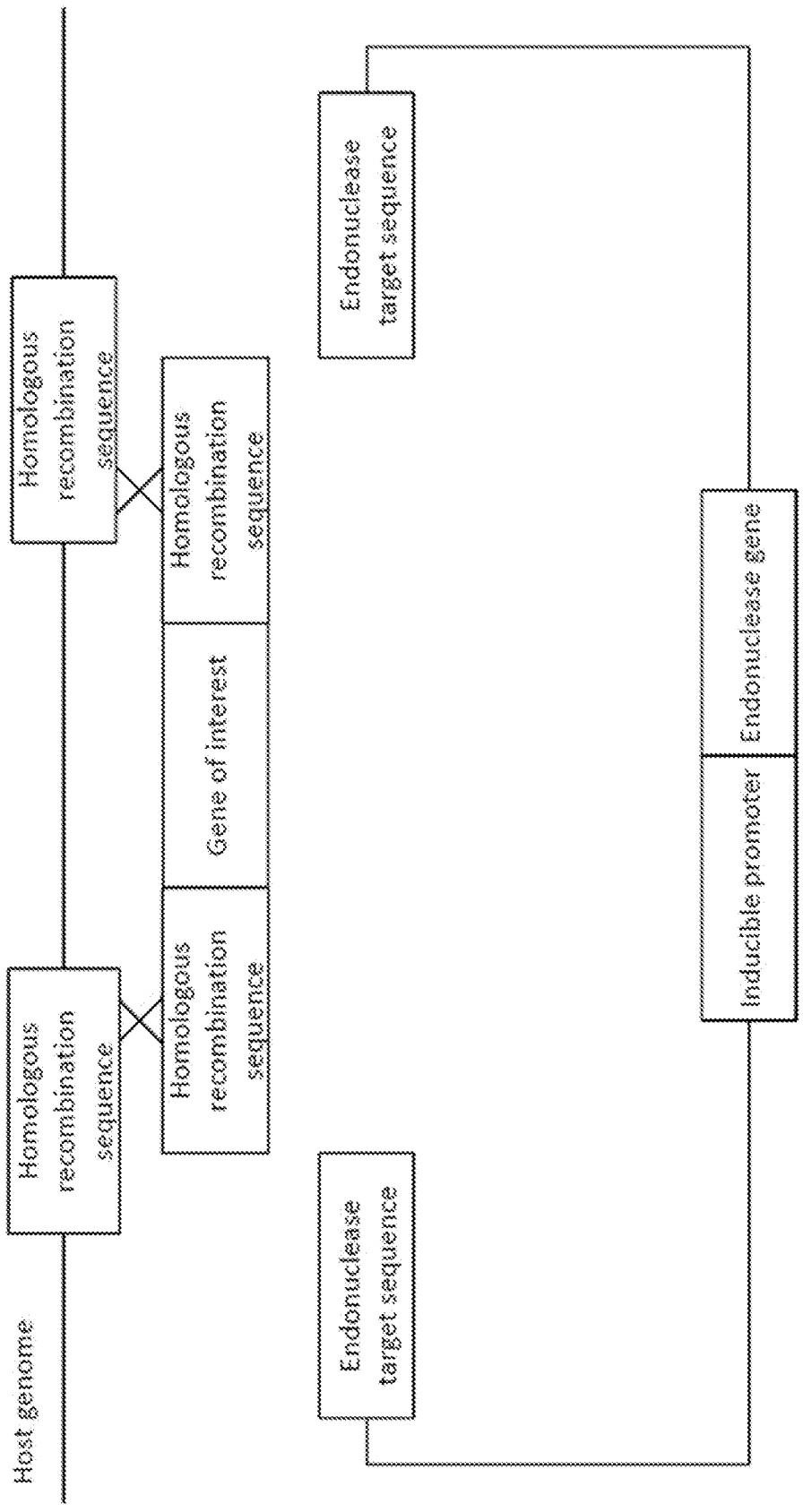
FIG. 1 is a configuration diagram schematically showing a mechanism of incorporating a gene of interest into a genome according to the method for producing a transformant and the transformation method according to the present disclosure.

At this time, the gene of interest sandwiched with the pair of homologous recombination sequences is disposed such that it is sandwiched with a pair of endonuclease target sequences, so that the gene of interest sandwiched with the pair of homologous recombination sequences can be cleaved by endonuclease specifically recognizing the endonuclease target sequences. That is, as schematically shown in FIG. 1, a fragment cleaved from the plasmid by endonuclease is configured to have a pair of homologous recombination sequences at both ends, so that the gene of interest is sandwiched with the pair of homologous recombination sequences. As such, homologous recombination takes place between the pair of homologous recombination sequences and the host genome, and as a result, the gene of interest can be incorporated into the host genome.

Herein, the pair of endonuclease target sequences may have previously been disposed in the linear genome-introduced nucleic acid fragment, or may also have previously been disposed in the helper plasmid for transformation. Otherwise, one of the pair of endonuclease target sequences may have previously been disposed in the linear genome-introduced nucleic acid fragment, and the other endonuclease target sequence may have previously been disposed in the helper plasmid for transformation.

First Embodiment

Figure 2:
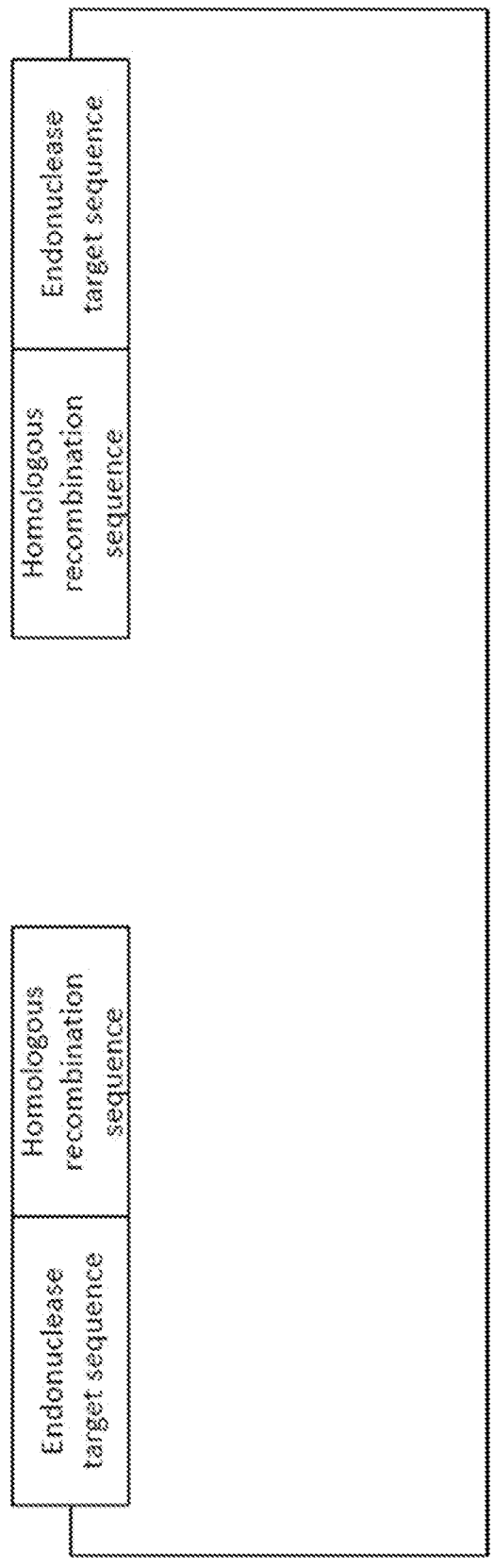
FIG. 2 is a configuration diagram schematically showing one configuration example of the helper plasmid for transformation according to the present disclosure.

Hereinafter, an embodiment in which a pair of endonuclease target sequences are disposed in a helper plasmid for transformation will be described. As shown in FIG. 2, the helper plasmid for transformation according to the present disclosure comprises a pair of homologous recombination sequences for incorporation of a linear genome-introduced nucleic acid fragment, and a pair of endonuclease target sequences disposed on the side opposite to the position into which the linear genome-introduced nucleic acid fragment is incorporated via the homologous recombination sequences. In other words, when the helper plasmid for transformation is cleaved at a position into which the above-described linear genome-introduced nucleic acid fragment is incorporated, so that it is converted to a linear plasmid, the linear plasmid has a pair of homologous recombination sequences at both ends thereof, and also has endonuclease target sequences following the respective homologous recombination sequences.

Figure 3:
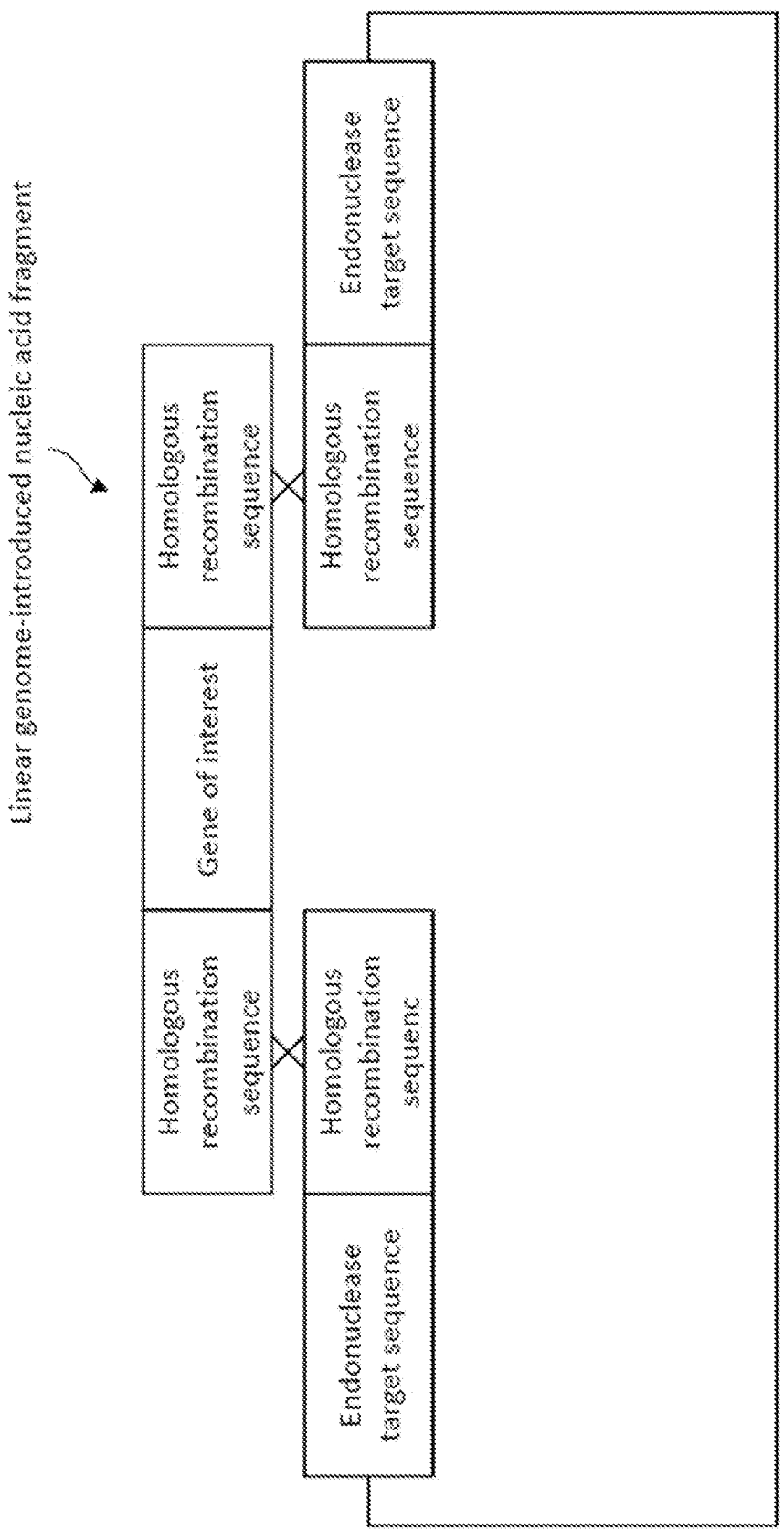
FIG. 3 is a configuration diagram schematically showing the helper plasmid for transformation according to the present disclosure and a linear genome-introduced nucleic acid fragment.

As shown in FIG. 3, a linear genome-introduced nucleic acid fragment comprising a gene of interest can be incorporated into the helper plasmid for transformation according to homologous recombination via the above-described pair of homologous recombination sequences. Herein, the linear genome-introduced nucleic acid fragment comprises a gene of interest and a pair of homologous recombination sequences that sandwich the gene of interest. That is to say, homologous recombination takes place between the homologous recombination sequences in the linear genome-introduced nucleic acid fragment and the homologous recombination sequences in the helper plasmid for transformation, so that the linear genome-introduced nucleic acid fragment can be incorporated into the helper plasmid for transformation. Moreover, homologous recombination takes place between the homologous recombination sequences in the linear genome-introduced nucleic acid fragment and a predetermined position on the genome, so that the gene of interest can be incorporated into the genome (see FIG. 1).

The term "a gene of interest" means a nucleic acid to be introduced into a host genome. Accordingly, such a gene of interest is not limited to a nucleotide sequence encoding a specific protein, and includes nucleic acids consisting of all types of nucleotide sequences, such as a nucleotide sequence encoding siRNA, etc., the nucleotide sequence of a transcriptional regulatory region that regulates the transcription period of a transcriptional product and the production amount thereof, such as a promoter or an enhance, and a nucleotide sequence encoding transfer RNA (tRNA), ribosome RNA (rRNA), etc.

Moreover, such a gene of interest is incorporated into the above-described site in an expressible state in some embodiments. The term "in an expressible state" means that a gene of interest has previously been linked to a predetermined promoter, such that the gene of interest can be expressed under the control of the promoter in a host organism.

Furthermore, to such a gene of interest, a promoter and a terminator, and as desired, a cis element such as an enhancer, a splicing signal, a poly A addition signal, a selective marker, a ribosomal binding sequence (SD sequence), and the like can be linked. Examples of the selective marker may include antibiotic resistance genes such as an ampicillin resistance gene, a kanamycin resistance gene, and a hygromycin resistance gene.

The term "a pair of homologous recombination sequences" means a pair of nucleic acid regions having homology to a certain region in a host genome. Such a pair of homologous recombination sequences in a linear genome-introduced nucleic acid fragment each cross with the host genome having homology with the homologous recombination sequences, so that a gene of interest sandwiched with the pair of homologous recombination sequences can be incorporated into the host genome. Accordingly, such a pair of homologous recombination sequences are not particularly limited to specific nucleotide sequences, and can be, for example, nucleotide sequences having high homology to the upstream region and downstream region of a certain gene present in the host genome. In this case, if homologous recombination takes place between the linear genome-introduced nucleic acid fragment and the host genome, the gene is deleted from the host genome. As such, the success or failure of homologous recombination can be determined by observing a phenotype caused by the deletion of the gene.

For example, such a pair of homologous recombination sequences can be a region upstream of the coding region of an ADE1 gene associated with an adenine biosynthesis pathway, and a region downstream of the coding region of the ADE1 gene. In this case, if homologous recombination takes place between the pair of homologous recombination sequences in the linear genome-introduced nucleic acid fragment and the host genome, an intermediate metabolite of adenine, 5-aminoimidazole riboside is accumulated, and a transformant is colored to red due to the polymerized polyribosylaminoimidazole. Accordingly, by detecting this red color, it can be determined that homologous recombination has taken place between the pair of homologous recombination sequences in the linear genome-introduced nucleic acid fragment and the host genome.

Herein, the pair of homologous recombination sequences in the linear genome-introduced nucleic acid fragment have high sequence identity to the recombination region in the host genome, to such an extent that they can be homologously recombined (can cross) with one another. The identity between the nucleotide sequences of individual regions can be calculated using conventionally known sequence comparison software "blastn", etc. The nucleotide sequences of individual regions may have an identity of 60% or more, and the sequence identity is 80% or more in some embodiments, 90% or more in some other embodiments, 95% or more in some other embodiments, and 99% or more in some other embodiments.

Further, such a pair of homologous recombination sequences in the linear genome-introduced nucleic acid fragment may have the same length, or may have each different lengths. The lengths of such a pair of homologous recombination sequences in the linear genome-introduced nucleic acid fragment are not particularly limited, as long as the lengths are sufficient for possible homologous recombination (possible crossing). The length of each of the pair of homologous recombination sequences is, for example, 0.1 kb to 3 kb in some embodiments, or 0.5 kb to 3 kb in some embodiments, or 0.5 kb to 2 kb in some other embodiments.

By the way, the helper plasmid for transformation according to the present disclosure has a pair of homologous recombination sequences for incorporation of the aforementioned linear genome-introduced nucleic acid fragment. The homologous recombination sequence of the helper plasmid for transformation may cause homologous recombination with the homologous recombination sequence of the linear genome-introduced nucleic acid fragment, and may have a length identical to or different from the homologous recombination sequence of the linear genome-introduced nucleic acid fragment.

The homologous recombination sequence of the helper plasmid for transformation is a nucleotide sequence having homology to the homologous recombination sequence of the linear genome-introduced nucleic acid fragment. The length of the homologous recombination sequence of the present helper plasmid may be, for example, 30 b to 300 b, and may be 40b to 200 b in some embodiments, and 50 b to 100 b in some other embodiments.

Moreover, in the helper plasmid for transformation according to the present disclosure, a pair of homologous recombination sequences for incorporation of a linear genome-introduced nucleic acid fragment means both a pair of homologous recombination sequences capable of direct homologous recombination with a pair of homologous recombination sequences in the linear genome-introduced nucleic acid fragment, and a pair of homologous recombination sequences capable of indirect homologous recombination with a pair of homologous recombination sequences in the linear genome-introduced nucleic acid fragment via one or more linear nucleic acid fragments. Herein, one or more linear nucleic acid fragments mean one nucleic acid fragment or a plurality of nucleic acid fragments that are combined with one another according to homologous recombination, in which one end of the fragment has a sequence capable of performing homologous recombination with the homologous recombination sequence of a helper plasmid for transformation, and the other end thereof has a sequence capable of performing homologous recombination with the homologous recombination sequence of a linear genome-introduced nucleic acid fragment.

Furthermore, the helper plasmid for transformation according to the present disclosure has endonuclease target sequences that follow the aforementioned pair of homologous recombination sequences. The endonuclease target sequence means a nucleotide sequence recognized by endonuclease.

The endonuclease is not particularly limited, and it broadly means an enzyme having an activity of recognizing a predetermined nucleotide sequence and cleaving double-stranded DNA. Examples of the endonuclease may include restriction enzymes, homing endonuclease, Cas9 nuclease, meganuclease (MN), zinc finger nuclease(ZFN), and transcriptional activation-like effector nuclease (TALEN). Moreover, the term "homing endonuclease" includes both endonuclease encoded by an intron (with the prefix "I-") and endonuclease included in an intein (with the prefix "PI-"). More specific examples of the homing endonuclease may include I-Ceu I, I-Sce I, I-Onu I, PI-Psp I, and PI-Sce I. Besides, target sequences specifically recognized by these specific endonucleases, namely, endonuclease target sequences are known, and a person skilled in the art could appropriately acquire such endonuclease target sequences.

Figure 4:
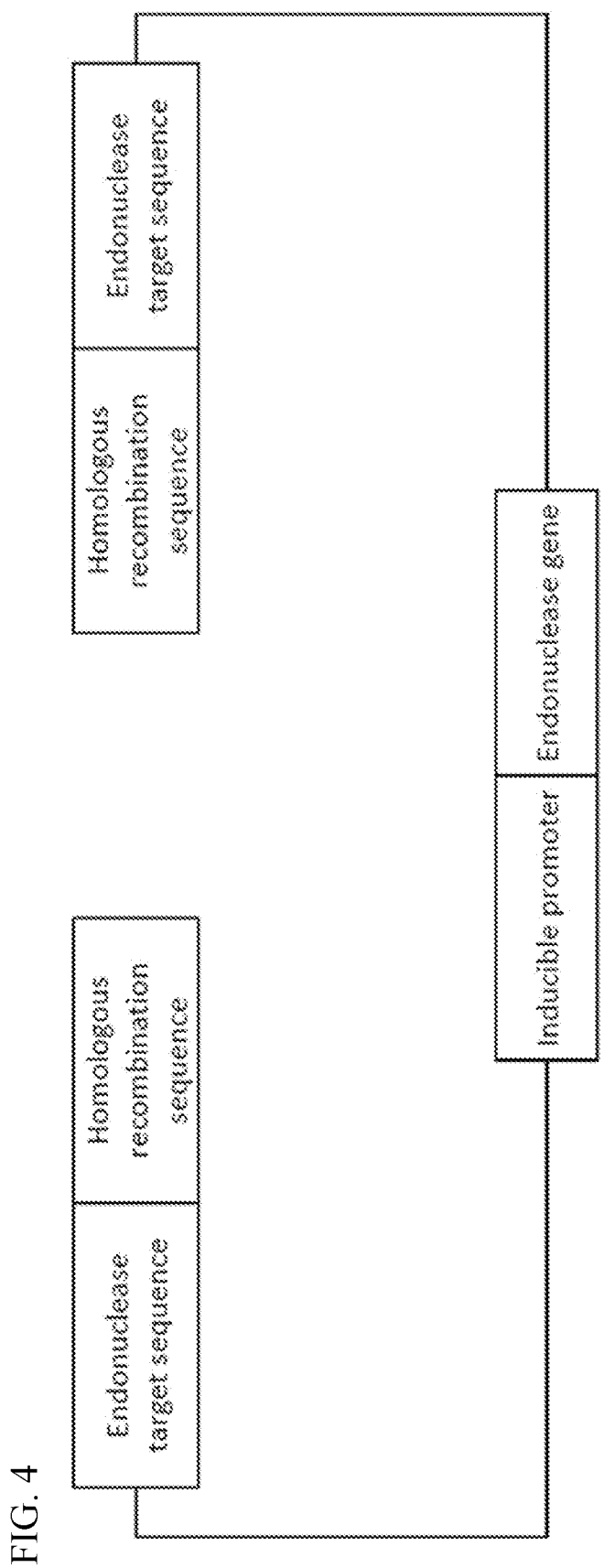
FIG. 4 is a configuration diagram schematically showing another configuration example of the helper plasmid for transformation according to the present disclosure.

Moreover, as shown in FIG. 4, the helper plasmid for transformation according to the present disclosure may comprise an inducible promoter and an endonuclease gene. For the expression of an endonuclease gene, not only an inducible promoter, but also a constant expression promoter may be used.

This endonuclease gene encodes an enzyme having an activity of specifically recognizing the aforementioned pair of endonuclease target sequences and cleaving the double strands. That is, examples of the endonuclease gene may include a restriction enzyme gene, a homing endonuclease gene, a Cas9 nuclease gene, a meganuclease gene, a zinc finger nuclease gene, and a transcriptional activation-like effector nuclease gene.

The inducible promoter means a promoter having the function of inducing expression under specific conditions. Examples of the inducible promoter may include, but are not particularly limited to, a promoter inducing expression in the presence of a specific substance, a promoter inducing expression under specific temperature conditions, and a promoter inducing expression in response to various types of stresses. The used promoter can be selected, as appropriate, depending on a host to be transformed.

Examples of the inducible promoter may include galactose inducible promoters such as GAL1 and GAL10, Tet-on/Tet-off system promoters inducing expression by addition or removal of tetracycline or a derivative thereof, and promoters of genes encoding heat shock proteins (HSP) such as HSP10, HSP60 and HSP90. In addition, as such an inducible promoter, a CUP1 promoter that activates by addition of copper ions can also be used. Furthermore, when the host is a prokaryotic cell such as *Escherichia coli*, examples of the inducible promoter may include a lac promoter inducing expression with IPTG, a cspA promoter inducing expression by cold shock, and an araBAD promoter inducing expression with arabinose.

Further, the method of controlling the expression of an endonuclease gene is not limited to a method of using a promoter such as an inducible promoter or a constant expression promoter, and for example, a method of using DNA recombinase may be applied. An example of the method of turning the expression of a gene ON and OFF may be a FLEx switch method (A FLEX Switch Targets Channelrhodopsin-2 to Multiple Cell Types for Imaging and Long-Range Circuit Mapping. Atasoy et al., The Journal of Neuroscience, 28, 7025-7030, 2008.). According to the FLEx switch method, recombination to change the direction of a promoter sequence is caused by DNA recombinase, so that the expression of a gene can be turned ON and OFF.

On the other hand, the helper plasmid for transformation according to the present disclosure can be produced based on a conventionally known, available plasmid. Examples of such a plasmid may include: YCp-type *Escherichia coli*-yeast shuttle vectors, such as pRS413, pRS414, pRS415, pRS416, YCp50, pAUR112, or pAUR123; YEp-type *Escherichia coli*-yeast shuttle vectors, such as pYES2 or YEp13; YIp-type *Escherichia co/i*-yeast shuttle vectors, such as pRS403, pRS404, pRS405, pRS406, pAUR101, or pAUR135; *Escherichia coli*-derived plasmids (e.g., ColE-type plasmids, such as pBR322, pBR325, pUC18, pUC19, pUC118, pUC119, pTV118N, pTV119N, pBluescript, pHSG298, pHSG396 or pTrc99A; p15A-type plasmids, such as pACYC177 or pACYC184; pSC101-type plasmids, such as pMW118, pMW119, pMW218 or pMW219; etc.); *Agrobacterium*-derived plasmids (e.g., pBI101, etc.); and *Bacillus subtilis*-derived plasmid (e.g., pUB110, pTP5, etc.).

The helper plasmid for transformation according to the present disclosure may further comprise a replication origin, an autonomously replicating sequence (ARS), and a centromere sequence (CEN). The helper plasmid for transformation comprises these elements, so that it can stably replicate after it has been introduced into a host cell. In addition, the helper plasmid for transformation according to the present disclosure may comprise a selective marker. The selective marker is not particularly limited, and examples of the selective marker may include a drug resistance marker gene and an auxotrophic marker gene. The helper plasmid for transformation comprises these selective markers, so that a host cell, into which the helper plasmid for transformation has been introduced, can be efficiently selected.

By using the thus configured helper plasmid for transformation, a stable transformant, in which a gene of interest is incorporated into the genome, can be simply and efficiently produced. To produce a transformant, first, a linear genome-introduced nucleic acid fragment comprising a gene of interest and a helper plasmid for transformation are introduced into a host cell according to a common method. At this time, the linear genome-introduced nucleic acid fragment is incorporated into the helper plasmid for transformation according to homologous recombination to form a circular plasmid (see FIG. 3). Thereafter, as schematically shown in FIG. 1, the double stands of a pair of endonuclease target sequences are cleaved by endonuclease, so that a linear genome-introduced nucleic acid fragment comprising the gene of interest sandwiched with the pair of homologous recombination sequences is cleaved out. A pair of homologous recombination sequences in the thus cleaved linear genome-introduced nucleic acid fragment cross with homologous recombination sequences in the host genome, and the gene of interest is then incorporated into the genome. Thereby, a stable transformant, in which the gene of interest is incorporated into the genome, can be produced.

Herein, the method of introducing the linear genome-introduced nucleic acid fragment having a gene of interest and the helper plasmid for transformation into a host cell is not particularly limited, and conventionally known methods such as, for example, a calcium chloride method, a competent cell method, a protoplast or spheroplast method, or an electrical pulse method, can be used, as appropriate. Thereafter, when the helper plasmid for transformation has a selective marker, the host cell, into the helper plasmid for transformation has been introduced, can be selected using the selective marker.

Moreover, to allow endonuclease to express under the control of an inducible promoter, conditions are determined, as appropriate, depending on the type of the inducible promoter. For example, when a galactose inducible promoter such as GAL1 or GAL10 is used as such an inducible promoter, galactose is added into a medium for use in the culture of the host cell into which the helper plasmid for transformation has been introduced, or the host cell is transferred into a galactose-containing medium and is then cultured, so that the expression of the endonuclease can be induced. On the other hand, when a promoter of a gene encoding a heat shock protein (HSP) is used as such an inducible promoter, heat shock is applied, at a desired timing, to the host cell into which the helper plasmid for transformation has been introduced, upon the culture of the host cell, so that the expression of the endonuclease can be induced at the desired timing.

It may also be possible to perform the treatment of introducing the linear genome-introduced nucleic acid fragment and the helper plasmid for transformation into a host cell under conditions in which an inducible promoter induces expression, so that endonuclease may be expressed under the control of the inducible promoter. In this case, the treatment of converting the conditions to expression induction conditions is not necessary, and thus, a transformant can be obtained more simply.

Furthermore, in the aforementioned helper plasmid for transformation, when the pair of homologous recombination sequences are set to be nucleotide sequences having high homology to the upstream region and downstream region of a predetermined gene, a linear genome-introduced nucleic acid fragment containing a gene of interest is incorporated into the genome according to homologous recombination, and at the same time, the predetermined gene is deleted from the genome. Accordingly, by observing a phenotype caused by the deletion of the predetermined gene, whether or not the linear genome-introduced nucleic acid fragment containing a gene of interest has been incorporated into the genome can be determined. For example, when an ADE1 gene is utilized as such a predetermined gene, if the linear genome-introduced nucleic acid fragment containing a gene of interest is incorporated into the genome, the ADE1 gene is deleted from the genome. As a result, 5-aminoimidazole riboside is accumulated in the host, and a transformant is colored to red due to the polymerized polyribosylaminoimidazole. Accordingly, by detecting this red color, it can be determined that the linear genome-introduced nucleic acid fragment containing a gene of interest has been incorporated into the genome of the host.

It is to be noted that, in the aforementioned example, the helper plasmid for transformation is configured to have an inducible promoter and an endonuclease gene, but that the helper plasmid for transformation according to the present disclosure may also be configured not to have such an inducible promoter and an endonuclease gene. In this case, an expression vector having an inducible promoter and an endonuclease gene may be prepared, separately, and the expression vector, together with the linear genome-introduced nucleic acid fragment comprising a gene of interest and the helper plasmid for transformation according to the present disclosure, may be introduced into a host cell. Even in this case, in the host cell into which the expression vector having an inducible promoter and an endonuclease gene, the linear genome-introduced nucleic acid fragment, and the helper plasmid for transformation have been introduced, the endonuclease gene is expressed under the control of the inducible promoter, so that, as shown in FIG. 1, a linear genome-introduced nucleic acid fragment containing the gene of interest sandwiched with a pair of homologous recombination sequences can be cleaved out, and a transformant, in which the gene of interest is incorporated into the genome, can be produced.

Figure 5:
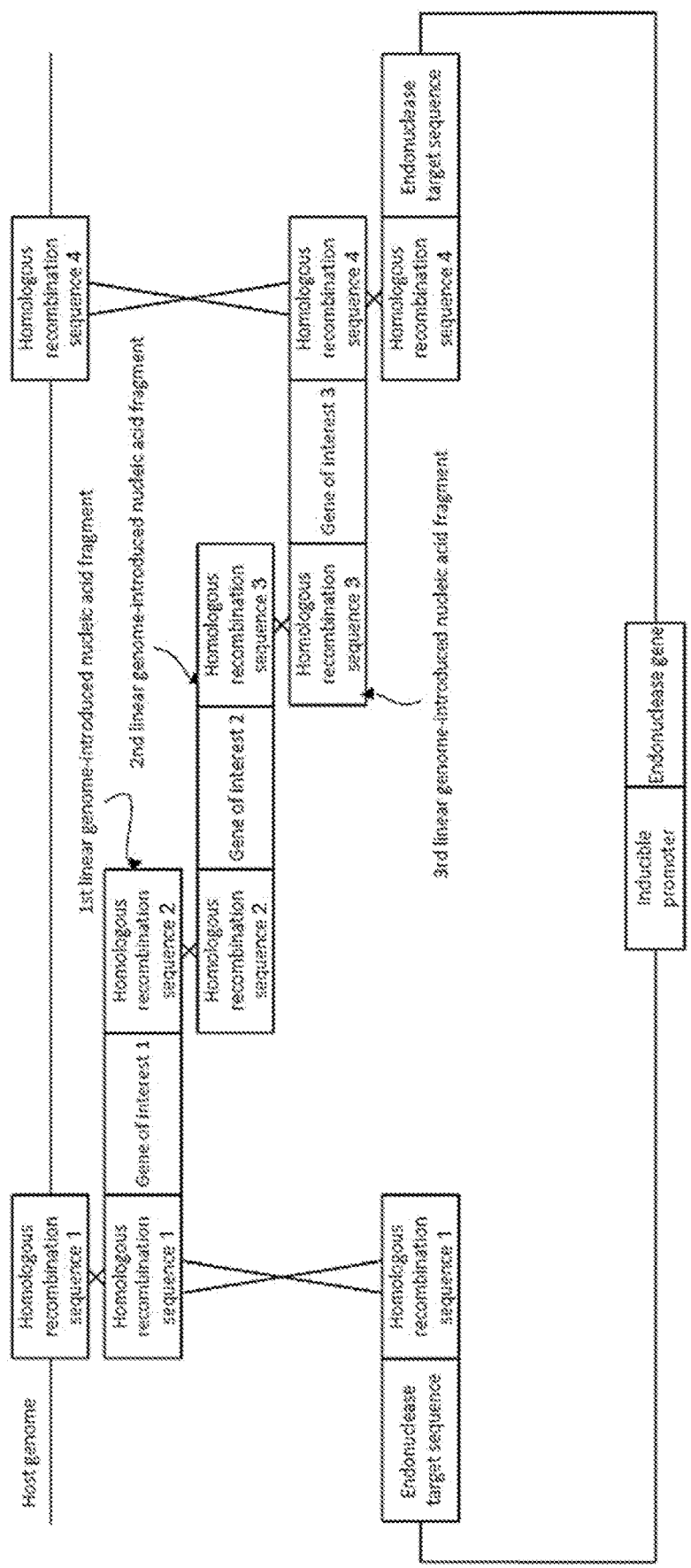
FIG. 5 is a configuration diagram schematically showing a mechanism of incorporating a plurality of genes of interest into a genome, using the helper plasmid for transformation according to the present disclosure.

On the other hand, by using the helper plasmid for transformation according to the present disclosure, a plurality of linear genome-introduced nucleic acid fragments can be disposed in series, and can be incorporated into a host genome. If the plurality of linear genome-introduced nucleic acid fragments are assumed to be a first linear genome-introduced nucleic acid fragment to the $n^{th}$ linear genome-introduced nucleic acid fragment (wherein n is an integer of 2 or more), by performing homologous recombination between the 3'-terminal side of the $m^{th}$ linear genome-introduced nucleic acid fragment (wherein m is an integer satisfying $1 \leq m \leq n-1$) and the 5'-terminal side of the $m^{th}+1$ linear genome-introduced nucleic acid fragment, the aforementioned first to $n^{th}$ linear genome-introduced nucleic acid fragments can be combined to one another in this order as a result of the homologous recombination. As one example, as shown in FIG. 5, when the first to third linear genome-introduced nucleic acid fragments are incorporated into a host genome, the 3'-terminal side of the first linear genome-introduced nucleic acid fragment and the 5'-terminal side of the second linear genome-introduced nucleic acid fragment are set to be homologous recombination sequences 2, and the 3'-terminal side of the second linear genome-introduced nucleic acid fragment and the 5'-terminal side of the third linear genome-introduced nucleic acid fragment are set to be homologous recombination sequences 3, so that the first to third linear genome-introduced nucleic acid fragments can be combined to one another in this order according to homologous recombination. A fragment obtained by combining the first to third linear genome-introduced nucleic acid fragments to one another is incorporated into a helper plasmid for transformation and a host genome according to homologous recombination occurring between the helper plasmid for transformation and the host genome via homologous recombination sequences 1 and homologous recombination sequences 4.

By the way, in order to dispose a plurality of linear genome-introduced nucleic acid fragments in series according to homologous recombination, a homologous recombination sequence is set between the linear genome-introduced nucleic acid fragments adjacent to each other. Such a homologous recombination sequence may have homologous recombination with a homologous recombination sequence of the adjacent linear genome-introduced nucleic acid fragment, and may have a length identical to or different from the homologous recombination sequence of the adjacent linear genome-introduced nucleic acid fragment. This homologous recombination sequence is a nucleotide sequence having homology to the homologous recombination sequence of the adjacent linear genome-introduced nucleic acid fragment. The length of this homologous recombination sequence may be, for example, 30 b to 300 b, and may be 40 b to 200 b in some embodiments, and 50 b to 100 b in some other embodiments.

As described above, by using the helper plasmid for transformation according to the present disclosure, a plurality of linear genome-introduced nucleic acid fragments can be disposed in series and can be incorporated into a host genome. Herein, such a plurality of linear genome-introduced nucleic acid fragments may each have a gene of interest, or only some linear genome-introduced nucleic acid fragments thereof may have a gene of interest.

Besides, the transformation method using a helper helper plasmid for transformation according to the present disclosure and the method for producing a transformant are not particularly limited, and these methods can be applied to all types of host cells. Examples of the host cells may include: fungi such as filamentous fungi or yeasts; bacteria such as *Escherichia coli* or *Bacillus subtilis*; plant cells; and animal cells including mammals or insects. Among these, yeasts are used as host cells in some embodiments. The type of the yeast is not particularly limited, and examples thereof may include yeasts belonging to genus *Saccharomyces*, yeasts belonging to genus *Kluyveromyces*, yeasts belonging to genus *Candida*, yeasts belonging to genus *Pichia*, yeasts belonging to genus *Schizosaccharomyces*, and yeasts belonging to genus *Hansenula*. More specifically, the aforementioned methods can be applied to yeasts belonging to genus *Saccharomyces* such as *Saccharomyces cerevisiae*, *Saccharomyces bayanus*, or *Saccharomyces boulardii*.

Second Embodiment

Hereinafter, an embodiment in which a pair of endonuclease target sequences are disposed in a linear genome-introduced nucleic acid fragment comprising a gene of interest will be described. It is to be noted that, in the following explanation, the same terms as those used in the explanation regarding the first embodiment are used, so that detailed explanation regarding the configuration, etc. will be omitted.

Figure 6:
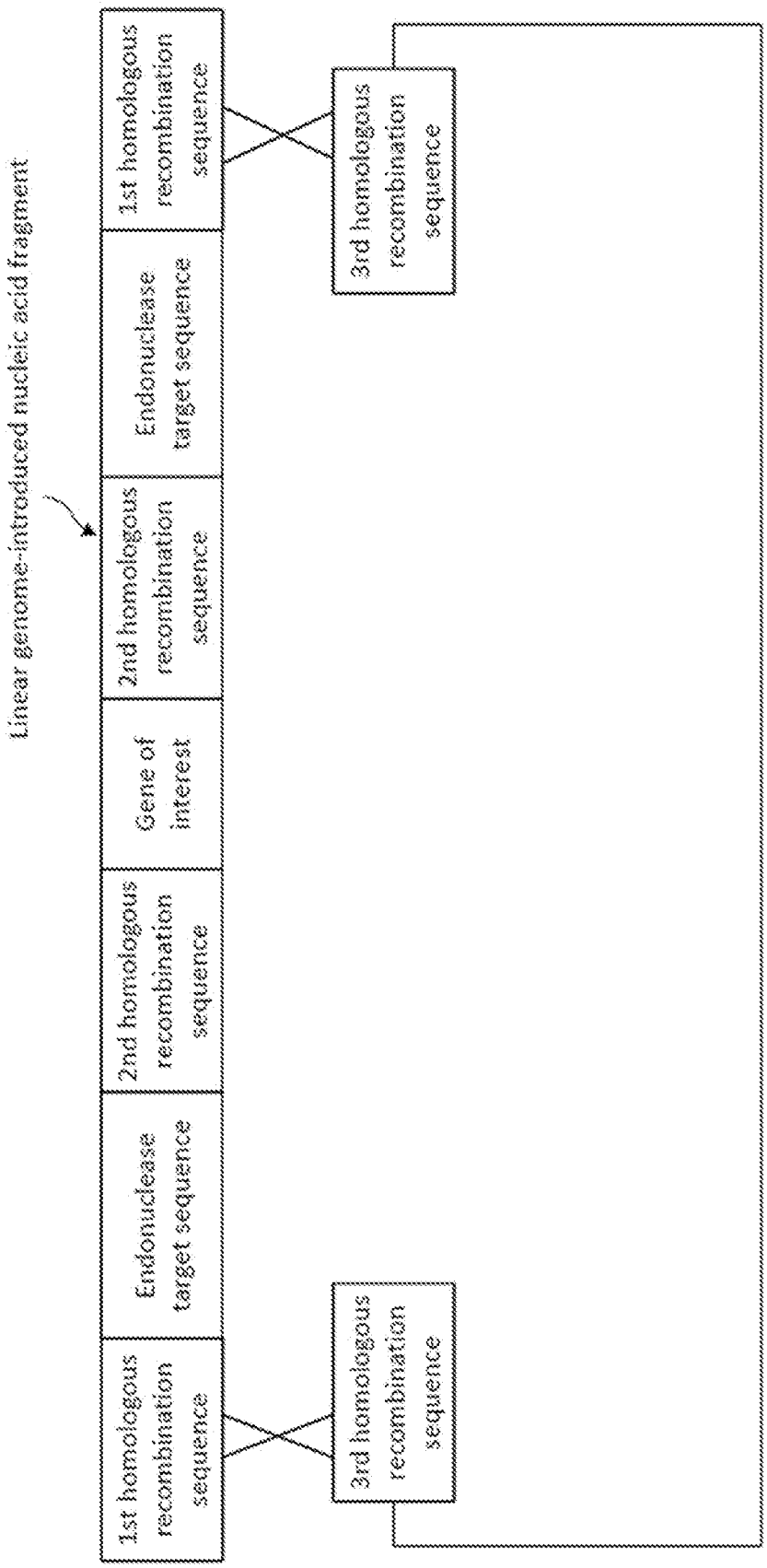
FIG. 6 is a configuration diagram schematically showing one configuration example of a linear genome-introduced nucleic acid fragment and a helper plasmid for transformation, given as a second embodiment.

In the second embodiment, as shown in FIG. 6, a linear genome-introduced nucleic acid fragment comprises a pair of first homologous recombination sequences capable of performing homologous recombination with a helper plasmid for transformation at both ends thereof, endonuclease target sequences inside of the first homologous recombination sequences, a pair of second homologous recombination sequences capable of performing homologous recombination with a host genome inside of the endonuclease target sequences, and a gene of interest inside of the pair of second homologous recombination sequences. In the present embodiment, the helper plasmid for transformation comprises a pair of third homologous recombination sequences for incorporation of the linear genome-introduced nucleic acid fragment. Moreover, as shown in FIG. 4 regarding the first embodiment, the helper plasmid for transformation may comprise an inducible promoter and an endonuclease gene downstream of the inducible promoter, although they are not shown in the figure.

Besides, even in the second embodiment, the pair of third homologous recombination sequences of the helper plasmid for transformation and the pair of first homologous recombination sequences of the linear genome-introduced nucleic acid fragment may directly perform homologous recombination, or they may indirectly perform homologous recombination via one or more linear nucleic acid fragments. Herein, one or more linear nucleic acid fragments mean one nucleic acid fragment or a plurality of nucleic acid fragments that are combined with one another according to homologous recombination, in which one end of the fragment has a sequence capable of performing homologous recombination with the third homologous recombination sequence of the helper plasmid for transformation, and the other end thereof has a sequence capable of performing homologous recombination with the first homologous recombination sequence of the linear genome-introduced nucleic acid fragment.

Figure 7:
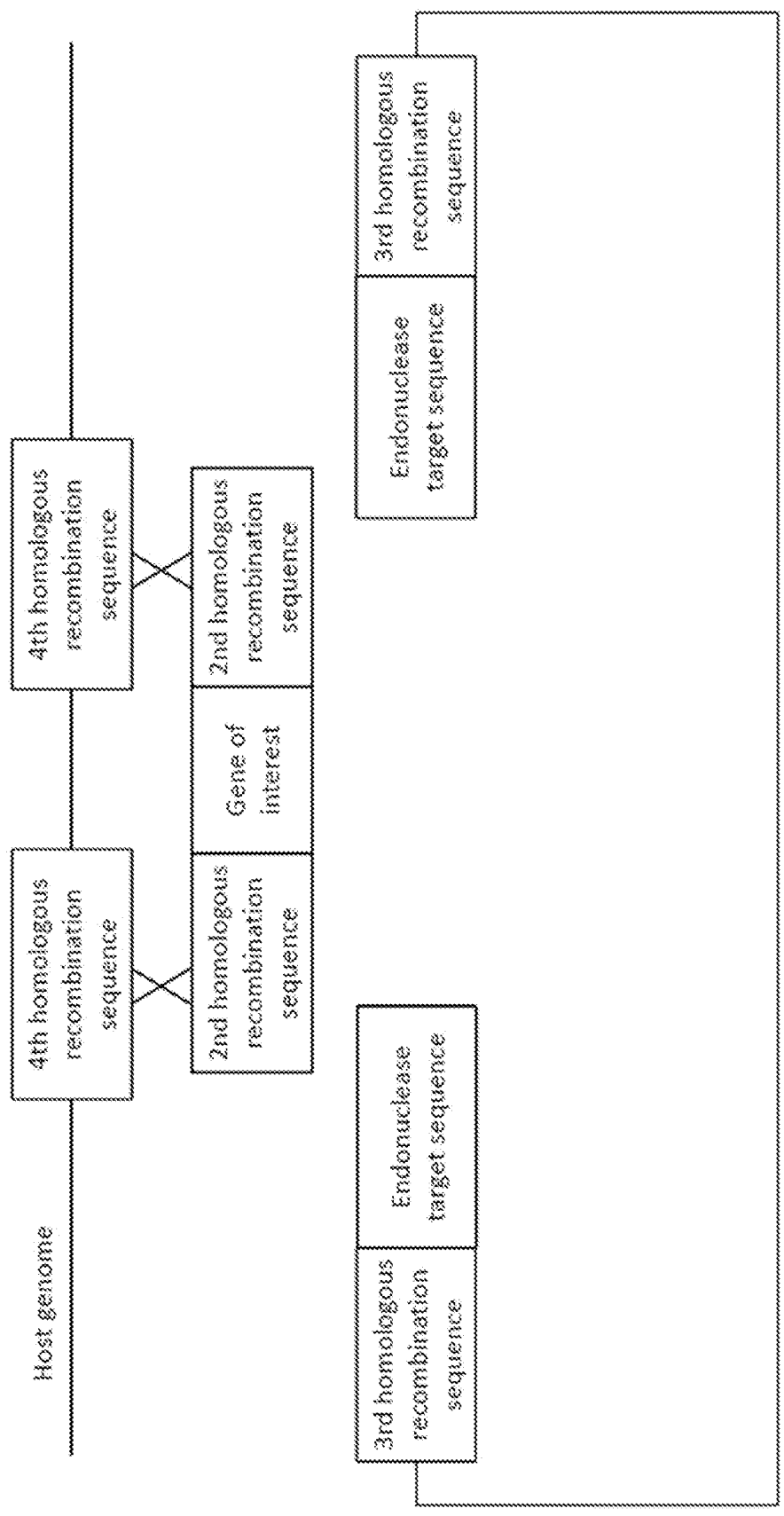
FIG. 7 is a configuration diagram schematically showing a mechanism of incorporating a gene of interest into a genome according to the method for producing a transformant and the transformation method, which is given as a second embodiment.

By using the thus configured linear genome-introduced nucleic acid fragment and helper plasmid for transformation, a stable transformant, in which a gene of interest is incorporated into the genome, can be simply and efficiently produced. To produce a transformant, first, the aforementioned linear genome-introduced nucleic acid fragment comprising a gene of interest and helper plasmid for transformation are introduced into a host cell according to a common method. At this time, homologous recombination takes place between the first homologous recombination sequence of the linear genome-introduced nucleic acid fragment and the third homologous recombination sequence of the helper plasmid for transformation, so that the linear genome-introduced nucleic acid fragment is incorporated into the helper plasmid for transformation to form a circular plasmid (see FIG. 7). Thereafter, as schematically shown in FIG. 7, the double stands of a pair of endonuclease target sequences are cleaved by endonuclease, so that a fragment containing the gene of interest sandwiched with the pair of second homologous recombination sequences is cleaved out. The pair of second homologous recombination sequences of the thus cleaved linear genome-introduced nucleic acid fragment cross with fourth homologous recombination sequences of the host genome, and the gene of interest is then incorporated into the genome. Thereby, a stable transformant, in which the gene of interest is incorporated into the genome, can be produced.

Figure 8:
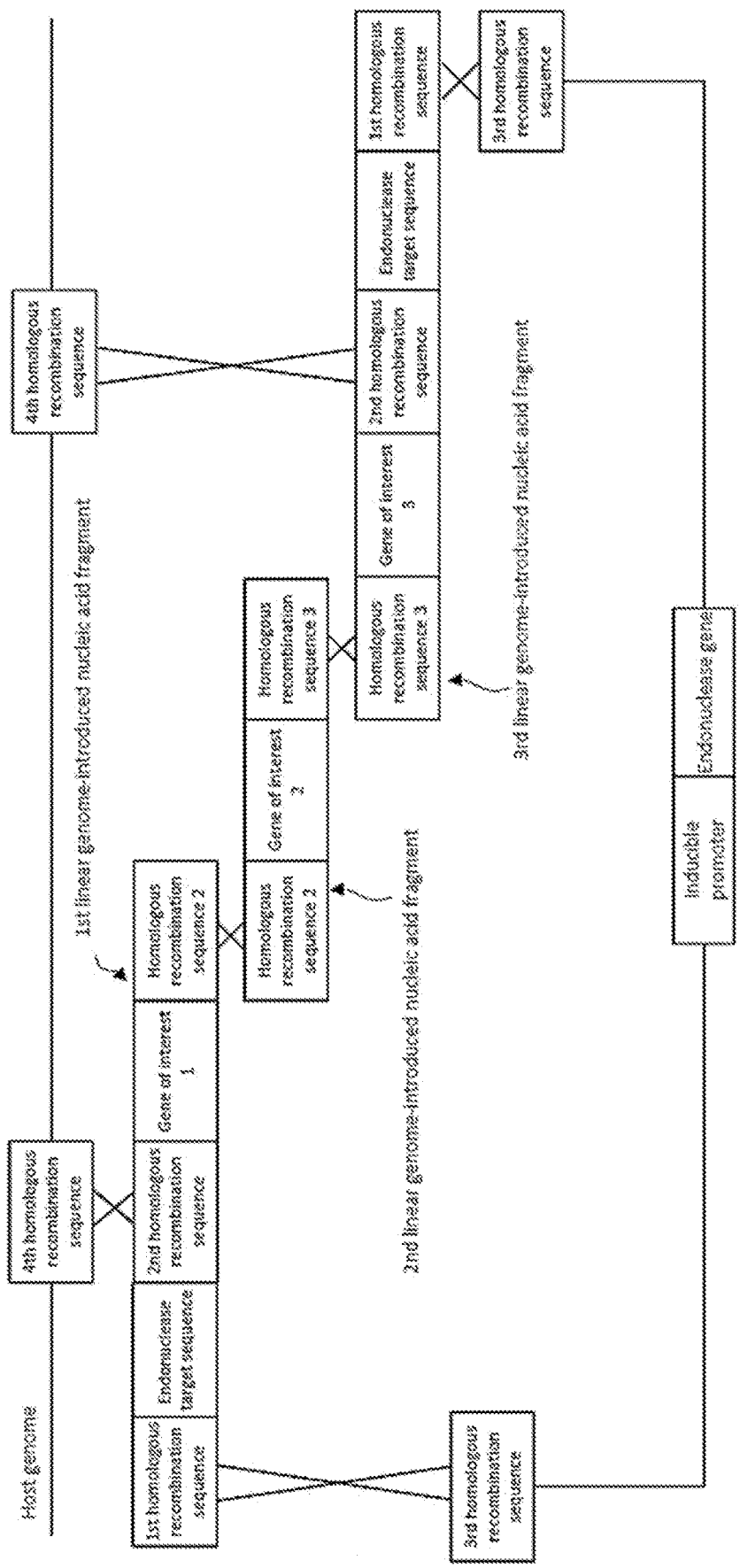
FIG. 8 is a configuration diagram schematically showing a mechanism of incorporating a plurality of genes of interest into a genome according to the method for producing a transformant and the transformation method, which is given as a second embodiment.

In addition, even in the present embodiment, a plurality of linear genome-introduced nucleic acid fragments can be disposed in series, and can be incorporated into a host genome. As one example, as shown in FIG. 8, when the first to third linear genome-introduced nucleic acid fragments are incorporated into a host genome, the 3-terminal side of the first linear genome-introduced nucleic acid fragment and the 5-terminal side of the second linear genome-introduced nucleic acid fragment are set to be homologous recombination sequences 2, and the 3-terminal side of the second linear genome-introduced nucleic acid fragment and the 5-terminal side of the third linear genome-introduced nucleic acid fragment are set to be homologous recombination sequences 3, so that the first to third linear genome-introduced nucleic acid fragments can be combined to one another in this order according to homologous recombination. The combined fragment is incorporated into a helper plasmid for transformation according to homologous recombination occurring between the first homologous recombination sequence of the fragment and the third homologous recombination sequence of the helper plasmid for transformation. Moreover, a fragment obtained by cleaving the endonuclease target sequence by endonuclease is incorporated into a host genome according to homologous recombination occurring between the second homologous recombination sequence and the fourth homologous recombination sequence of the genome.

EXAMPLES

Hereinafter, the present disclosure will be described in more detail in the following examples. However, these examples are not intended to limit the technical scope of the present disclosure.

Example 1

In the present example, a monoploid experimental yeast, S. cerevisiae BY4742, was used as a test yeast line.
<Production of Vectors>

The produced three types of vectors were: a YEp-type yeast shuttle vector pRS436(SAT)-P_GAL1-SCEI-T_CYC1-Sce-5U_ADE1-P_AgTEF1-G418-T_AgTEF1-3U_ADE1-Sce (see FIG. 9), comprising S. cerevisiae-derived homing endonuclease I-SceI (SCEI gene, NCBI Accession No. 854590) induced by galactose, and a sequence formed by inserting a DNA fragment containing a pair of homologous recombination sequences to be introduced into the genome between a pair of I-SceI target sequences (endonuclease target sequences); a YCp-type yeast shuttle vector pRS436cen(SAT)-P_GAL1-SCEI-T_CYC1-Sce-5U_ADE1-P_AgTEF1-G418-T_AgTEF1-3U_ADE1-Sce; and a YEp-type yeast shuttle vector pRS436(SAT)-P_GAL1-OnuIi-T_CYC1-Onu-5U_ADE1-P_AgTEF1-G418-T_AgTEF1-3U_ADE1-Onu, comprising Ophiostoma novo-ulmi subsp. americana-derived homing endonuclease I-OnuI gene (NCBI Accession No. AY275136.2) induced by galactose, and a sequence formed by inserting a DNA fragment containing a pair of homologous recombination sequences to be introduced into the genome between a pair of I-OnuI target sequences (endonuclease target sequences).

Regarding the vector pRS436(SAT)-P_GAL1-SCEI-T_CYC1-Sce-5U_ADE1-P_AgTEF1-G418-T_AgTEF1-3U_ADE1-Sce, a SCEI gene to which a GAL1 promoter and a CYC1 terminator had been added (a sequence into which the intron of a COX5B gene had been inserted, and in which codons in the whole length had been converted depending on the codon use frequency in the nuclear genome of the yeast; SEQ ID NOS: 1 and 2); a gene sequence containing a nourseothricin resistance gene (nat marker); as homologous recombination sequences to be introduced into the genome, the gene sequence in a region approximately 1000 bp upstream of the 5'-terminal side of an ADE1 gene (5U_ADE1) and the DNA sequence in a region approximately 950 bp downstream of the 3'-terminal side of the ADE1 gene (3U ADE1); and as a marker gene for homologous recombination, a gene sequence containing a G418 resistance gene (G418 marker), to which Ashbya gossypii-derived TEF1 promoter and TEF1 terminator had been added, were inserted into a vector prepared by removing a URA3 gene, a TDH3 promoter, and a CYC1 terminator from pRS436GAP vector (NCBI Accession No. AB304862) used as a YEp-type yeast shuttle vector. Besides, 5U_ADE1, 3U_ADE1, and the G418 marker were inserted between two homing endonuclease I-SceI target sequences, and could be cleaved by the SCEI gene added to the GAL1 promoter that was induced in a medium containing galactose as a carbon source.

Individual DNA sequences can be amplified by PCR. To bind individual DNA fragments to each other, there were synthesized primers, to each of which a DNA sequence was added to overlap with a DNA sequence adjacent thereto by approximately 15 bp (Table 1). Using these primers, a DNA fragment of interest was amplified with the genome of S. cerevisiae OC-2 strain or synthetic DNA used as a template, and the DNA fragments were successively bound to each other, using IN-FUSION® HD CLONING KIT, etc. The resultant was cloned into the pRS436GAP vector to produce a final plasmid of interest.

pRS436cen(SAT)-P_GAL1-SCEI-T_CYC1-Sce-5U_ADE1-P_AgTEF1-G418-T_AgTEF1-3U_ADE1-Sce is a vector, in which a 2-μm plasmid-derived replication origin is deleted from pRS436(SAT)-P_GAL1-SCEI-T_CYC1-Sce-5U_ADE1-P_AgTEF1-G418-T_AgTEF1-3U_ADE1-Sce, and instead of it, an autonomously replicating sequence (ARS) and a centromere sequence(CEN) are inserted therein, and the copy number in a cell is retained to be 1 copy. The present vector was produced by amplifying DNA fragments of interest, using, as a template, RS436(SAT)-P_GAL1-SCEI-T_CYC1-Sce-5U_ADE1-P_AgTEF1-G418-T_AgTEF1-3U_ADE1-Sce or the genome of S. cerevisiae OC-2 strain (the used primers are shown in Table 1), and then binding the DNA fragments with one another using IN-FUSION® HD CLONING KIT, etc.

pRS436(SAT)-P_GAL1-OnuIi-T_CYC1-Onu-5U_ADE1-P_AgTEF1-G418-T_AgTEF1-3U_ADE1-Onu is a vector, in which the SCEI gene of pRS436(SAT)-P_GAL1-SCEI-T_CYC1-Sce-5U_ADE1-P_AgTEF1-G418-T_AgTEF1-3U_ADE1-Sce is substituted with an I-OnuI gene and further, the I-SceI target sequence is substituted with an I-OnuI target sequence. The present vector was produced by amplifying DNA fragments of interest, using as a template, RS436(SAT)-P_GAL1-SCEI-T_CYC1-Sce-5U_ADE1-P_AgTEF1-G418-T_AgTEF1-3U_ADE1-Sce or a synthetic I-OnuI gene (the used primers are shown in Table 1), and then binding the DNA fragments with one another using IN-FUSION® HD CLONING KIT, etc.

TABLE 1

| Amplified DNA fragment | Primer sequence (5'-3') | SEQ ID NO: |
|---|---|---|
| pRS436(SAT)- P_GAL1-SCEI-T_CYC1-Sce-5U_ADE1-P_AgTEF1-G418-T_AgTEF1-3U_ADE1-Sce | | |
| GAL1 promoter | ACGGATTAGAAGCCGCCGAG | 3 |
|  | GGTTTTTTCTCCTTGACGTTAAAGTATAG | 4 |
| COX5B intron | TCAAGGAGAAAAACCAGCATGTATAACAAACACTGATTTTTGTTTTG | 5 |
|  | TCTTAATGTTTTTCACTGCAAAACTTGTGCTTGTACAC | 6 |
| SCEI | TGAAAAACATTAAGAAAAACCAAGTTATG | 7 |
|  | GCGTGACATAACTAATCATTTCAAGAAGGTTTCGGAG | 8 |
| CYC1 terminator (including I-SceI target sequence) | STTAGTTATGTCACGCTTACATTCACG | 9 |
|  | AATTGCCCCGACTCATATTACCCTGTTATCCCTAAGCTTGCAAATTAAAGCCTTCGAGCG | 10 |
| 5U_ADE1 | ATGAGTCGGGCAATTCCG | 11 |
|  | CTGGGCCTCCATGTCTATCGTTAATATTTCGTATGTGTATTCTTTG | 12 |
| TEF1 promoter derived from Ashbya gossypli | GACATGGAGGCCCAGAATAC | 13 |
|  | GGTTGTTTATGTTCGGATGTGATG | 14 |
| G418 | CGAACATAAACAACCATGGGTAAGGAAAAGACTCACGTTTC | 15 |
|  | TATTGTCAGTACTGATTAGAAAAACTCATCGAGCATCAAATGAAAC | 16 |
| TEF1 promoter derived from Ashbya gossypli | TCAGTACTGACAATAAAAAGATTCTTGTTTTCAAG | 17 |
|  | CAGTATAGCGACCAGCATTCACATACG | 18 |
| TEF1 promoter (including portion of LoxP sequence) | ATAGCATACATTATACGAAGTTATCCCACACACCATAGCTTCAAAATG | 19 |
|  | CACCGAAATCTTCATCCCTTAGATTAGATTGCTATGC | 20 |
| 3U_ADE1 (including I-SceI target sequence) | GCTGGTCGCTATACTGCGTGATTTACATATACTACAAGTCG | 21 |
|  | AAAAACATAAGACAAATTACCCTGTTATCCCTATGACCGGATGAAACC | 22 |
| pRS436 (including 2μ replication origin) | GGGATAACAGGGGTAATGGTACCCAATTCGCCCTATAG | 23 |
|  | TACCGCACAGATGCGTAAGG | 24 |
| LEU2 terminator | TTACGCATCTGTGCGGTAAGGAATCATAGTTTCATGATTTTCTG | 25 |
|  | CAGGATGACGCCTAAAAAGATTCTCTTTTTTTATGATATTTGTAC | 26 |
| nourseothricin resistance gene | TTAGGCGTCATCCTGTGCTC | 27 |
|  | CACACTAAATTAATAATGAAGATTTCGGTGATCCC | 28 |
| CYC1 promoter | TATTAATTTAGTGTGTGTATTTGTGTTTGTGTG | 29 |
|  | GCAGATTGTACTGAGAGTACGACATCGTCGAATATGATTC | 30 |
| pRS436 (including ampicillin resistance gene and ColE1 replication origin) | ACTCTCAGTACAATCTGCTCTGATGC | 31 |
|  | CGGCTTCTAATCCGTGCTCCAGCTTTTGTTCCCTTTAG | 32 |
| pRS436cen(SAT)-P_GAL1-SCEI-T_CYC1-Sce-5U_ADE1-P_AgTEF1-G418-T_AgTEF1-3U_ADE1-Sce | | |
| Sequence other than GAL1 promoter | TCAAGGAGAAAAAACCAGCATGTATAACAAACACTGATTTTTGTTTTG | 33 |
|  | CGGCTTCTAATCCGTGCTCCAGCTTTTGTTCCCTTTAG | 34 |
| GAL1 promoter | GGTCCTTTTCATCACGTGCTA | 35 |
|  | GGTTTTTTCTCCTTGACGTTAAAGTATAG | 36 |
| pRS436(SAT)-P_GAL1-OnuIi-T_CYC1-Onu-5U_ADE1-P_AgTEF1-G418-T_AgTEF1-3U_ADE1-Onu | | |
| Sequence excluding I-OnuI, 5U_ADE1, 3U_ADE1 and G418 marker | TTATCGATGATAAGCTGTCAAAGATG | 37 |
|  | TGGTTTTTTCTCCTTGACGTTAAAGTATAG | 38 |
| I-OnuI | TTATCGATGATAAGCTGTCAAAGATG | 39 |
|  | TCGGTTAGAGCGGATGTGGGGGGAGGGCGTGAATGTAAGCGTGAC | 40 |
| CYC1 terminator | ATCCGCTCTAACCGAAAAGG | 41 |
|  | AGCTTGCAAATTAAAGCCTTCG | 42 |
| 5U_ADE1, 3U_ADE1 and G418 marker sequence (including I-OnuI target sequence) | TTTAATTTGCAAGCTTTTCCACTTATTCAACCTTTTAATGAGTCGGGCAATTCCGAAG | 43 |
|  | GCTTATCATCGATAATAAAAGGTTGAATAAGTGGAAATGACCGGATGAAACCACCGG | 44 |

<Production of Linear Genome-Introduced Nucleic Acid Fragment for ADE1 Disruption>

Figure 9:
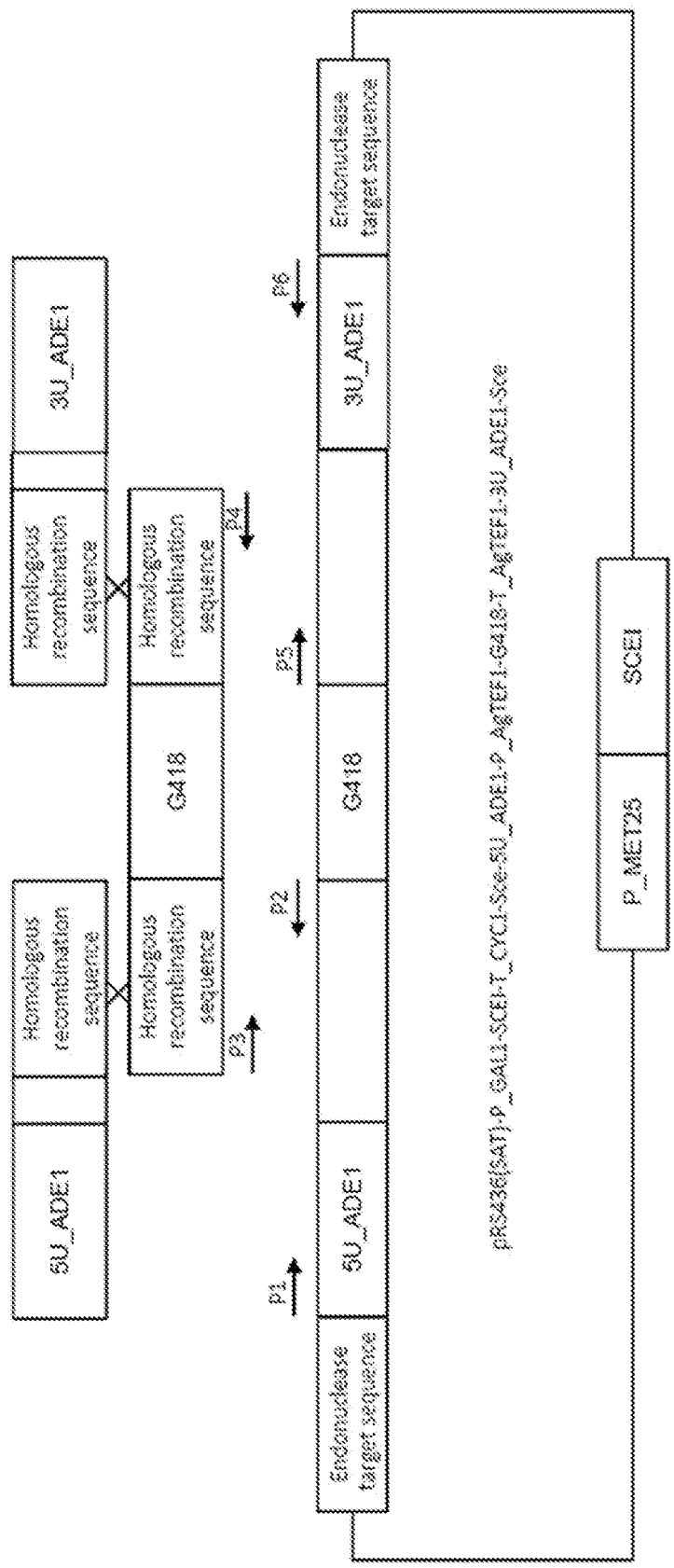
FIG. 9 is a configuration diagram schematically showing a scheme of amplifying the three types of linear genome-introduced nucleic acid fragments produced in the Examples.

In the present example, among the above produced vectors, the YEp-type yeast shuttle vector pRS436(SAT)-P_MET25-SCEI-T_CYC1-Sce-5U_ADE1-P_AgTEF1-G418-T_AgTEF1-3U_ADE1-Sce was used as a template, and the primers shown in Table 2 were also used, a fragment comprising the 5' homologous recombination sequence of an ADE1 gene, a fragment comprising the 3' homologous recombination sequence of an ADE1 gene, and a fragment of a G418 marker were amplified. More specifically, as schematically shown in FIG. 9, using the primers P1 and P2, the fragment comprising the 5' homologous recombination sequence of the ADE1 gene was amplified; using the primers P3 and P4, a fragment comprising a G418 marker was amplified; and using the primers P5 and P6, the fragment A comprising the 3' homologous recombination sequence of the ADE1 gene was amplified. Besides, the primers were designed so that individual primers were approximately 60 bp overlapped with one another. The nucleotide sequences of individual primers are shown in Table 2.

TABLE 2

| Amplified DNA fragment | Primer name | Primer sequence (5'-3') | SEQ ID NO: |
|---|---|---|---|
| Fragment including ADE1 5' homologous recombination sequence | P1 | ACGGATTAGAAGCCGCCGAG | 45 |
|  | P2 | TCATGCCCCTGAGCTGCG | 46 |
| Fragment including G416 marker | P3 | GACATGGAGGCCCAGAATAC | 47 |
|  | P4 | CAGTATAGCGACCAGCATTCACATACG | 48 |
| Fragment including ADE1 3' homologous recombination sequence | P5 | TTAAGTGCGCAGAAAGTAATATCATG | 49 |
|  | P6 | TGACCGGATGAAACCACC | 50 |

<Production of Helper Plasmid for Transformation>

Figure 10:
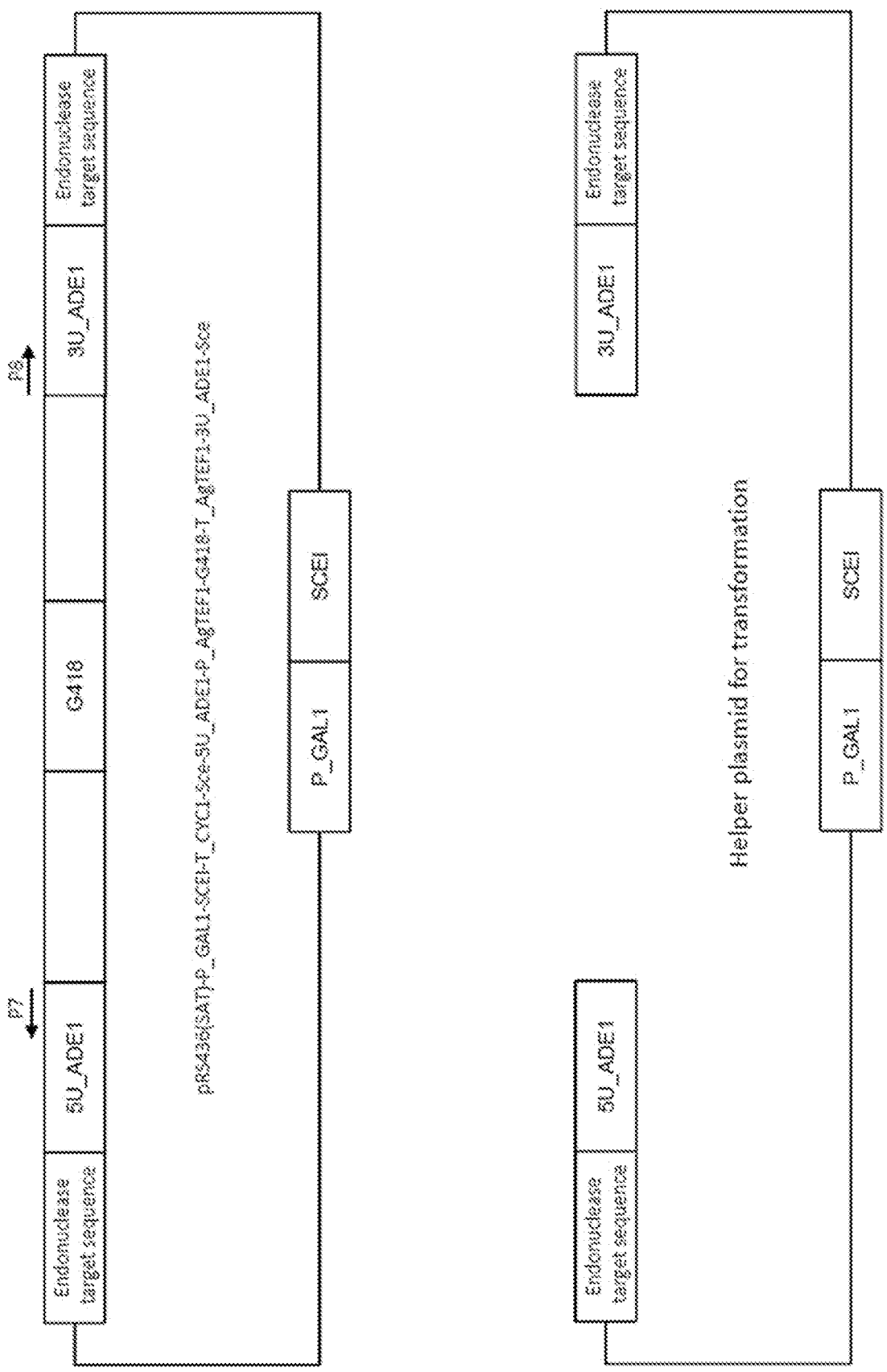
FIG. 10 is a configuration diagram schematically showing a scheme of amplifying the helper plasmid for transformation produced in the Examples.

In the present example, the above produced vector, namely, the YEp-type yeast shuttle vector pRS436(SAT)-P_GAL1-SCEI-T_CYC1-Sce-5U_ADE1-P_AgTEF1-G418-T_AgTEF1-3U_ADE1-Sce, the YCp-type yeast shuttle vector pRS436cen(SAT)-P_GAL1-SCEI-T_CYC1-Sce-5U_ADE1-P_AgTEF1-G418-T_AgTEF1-3U_ADE1-Sce, or the YEp-type yeast shuttle vector pRS436(SAT)-P_GAL1-OnuIi-T_CYC1-Onu-5U_ADE1-P_AgTEF1-G418-T_AgTEF1-3U_ADE1-Onu was used as a template, and also, the primers shown in Table 3, which were approximately 60 bp overlapped with a linear genome-introduced nucleic acid fragment comprising the 5' or 3' homologous recombination sequence of ADE1, were used to amplify a helper plasmid for transformation. As schematically shown in FIG. 10, more specifically, the helper plasmid for transformation was amplified by PCR using the primers P7 and P8. The nucleotide sequences of individual primers are shown in Table 3.

TABLE 3

| Amplified DNA fragment | Primer name | Primer sequence (5'-3') | SEQ ID NO: |
|---|---|---|---|
| Helper plasmid for transformation | P7 | GGTTTCAGATCACGATGGATAAC | 51 |
|  | P8 | GCAACAGTAAAAGGGATCAGC | 52 |

<Transformation Using Linear Genome-Introduced Nucleic Acid Fragment and Helper Plasmid for Transformation>

The above produced three types of linear genome-introduced nucleic acid fragments and the above produced helper plasmid for transformation were each used in a concentration of 2 fmol/μl to transform the S. cerevisiae BY4742 strain ($10^6$ cells/μl), and the thus transformed strain was then cultured in a YPGa (carbon source: 2% galactose) liquid medium for 7 hours. Thereafter, the cell concentration was measured using an absorption spectrophotometer, and the culture solution was then applied to a G418-containing YPGa agar medium ($10^6$ and $10^7$ cells/plate). The growing colonies were counted. Transformation was carried out according to the method of Akada et al. [Akada, R. et al. "Elevated temperature greatly improves transformation of fresh and frozen competent cells in yeast" BioTechniques 28 (2000): 854-856].

In a medium containing galactose, it is considered that homing endonuclease I-SceI would be induced, three types of linear genome-introduced nucleic acid fragments would be cut out in a ligated state, homologous recombination would take place in the ADE1 gene locus, and the ADE1 gene would be disrupted. The ADE1 gene is a gene of adenine biosynthesis pathway, and in the ADE1 gene-disrupted strain, 5-aminoimidazole riboside as an intermediate metabolite of adenine is accumulated, and the polymerized polyribosylaminoimidazole is colored to red. Hence, the ADE1 gene-disrupted strain can be easily distinguished. It is to be noted that the efficiency of homologous recombination in the ADE1 gene locus was calculated according to the following equation: ADE1 gene disruption efficiency (%)=Number of red colonies growing in agar medium/Number of cells dispersed on agar medium For the purpose of comparison, transformation was carried out without using the helper plasmid for transformation, but only using the above produced three types of linear genome-introduced nucleic acid fragments, and thereafter, the ADE1 gene disruption efficiency was calculated in the same manner as described above.

Results and Discussion

The results obtained by calculating the ADE1 gene disruption efficiency in the case of using the three types of linear genome-introduced nucleic acid fragments and the three types of helper plasmids for transformation, and in the case of only using the three types of linear genome-introduced nucleic acid fragments are shown in Table 4.

TABLE 4

|  | ADE1 gene disruption efficiency |
|---|---|
| Only 3 types of linear genome-introduced nucleic acid fragments | $2.2 \times 10^{-5}$ |
| Only 3 types of linear genome-introduced nucleic acid fragments + Helper plasmid for transformation: pRS436(SAT)-P_GAL1-SCEI-T_CYC1-Sce-5U_ADE1-P_AgTEF1-G418-T_AgTEF1-3U_ADE1-Sce | $5.3 \times 10^{-3}$ |
| Only 3 types of lineargenome-introduced nucleic acidfragments + Helper plasmid for transformation: pRS436cen(SAT)-P_GAL1-SCEI-T_CYC1-Sce-5U_ADE1-P_AgTEF1-G418-T_AgTEF1-3U_ADE1-Sce | $1.2 \times 10^{-3}$ |
| Only 3 types of linear genome-introduced nucleic acid fragments + Helper plasmid for transformation: pRS436(SAT)-P_GAL1-OnuIi-T_CYC1-Onu-5U_ADE1-P_AgTEF1-G418-T_AgTEF1-3U_ADE1-Onu | $2.0 \times 10^{-3}$ |

As is found from Table 4, when the helper plasmid for transformation was used, the ADE1 gene-disrupted strain was obtained with efficiency approximately 50 to 240 times higher than that in the case of only using the linear genome-introduced nucleic acid fragments. From these results, it was clarified that the efficiency of introducing a linear genome-introduced nucleic acid fragment into a genome can be improved by using a helper plasmid for transformation comprising a pair of homologous recombination sequences for introduction of a gene of interest into a host genome and a pair of endonuclease target sequences sandwiching the pair of homologous recombination sequences.

What is claimed is:

1. A method for producing a transformed host yeast comprising a circular plasmid formed by homologous recombination, the method comprising:
   introducing into a host yeast:
   (a) one or a plurality of linear nucleic acid fragments each comprising a gene of interest to be introduced into a predetermined position on a genome of the host yeast, and
   (b) a helper plasmid for transformation comprising a first homologous recombination sequence and a second homologous recombination sequence for incorporation of the linear nucleic acid fragments, a first and a second endonuclease target sequence, a gene encoding an endonuclease that specifically cleaves double strands of the first and the second endonuclease target sequences, a replication origin, and an autonomously replicating sequence (ARS),
   thereby producing a transformed host yeast comprising the circular plasmid, wherein said circular plasmid comprises: (i) the gene of interest, (ii) the first homologous recombination sequence, (iii) the first endonuclease target sequence upstream of the gene of interest, (iv) the second homologous recombination sequence, (v) the second endonuclease target sequence downstream of the gene of interest, and (vi) the gene encoding the endonuclease;
   culturing the transformed host yeast comprising the circular plasmid under a condition to express the gene encoding the endonuclease, such that the circular plasmid is cleaved at the first and the second endonuclease target sequences by the endonuclease to produce a cleavage fragment comprising (i) the gene of interest, (ii) the first homologous recombination sequence upstream of the gene of interest, and (iii) the second homologous recombination sequence downstream of the gene of interest, such that homologous recombination to introduce the gene of interest into the genome of the transformed host yeast takes place at the first and the second homologous recombination sequences of the cleavage fragment; and
   selecting a transformed host yeast comprising the gene of interest incorporated in the predetermined position in the host genome and expressing the gene of interest.

2. The method according to claim 1, wherein the endonuclease gene is a homing endonuclease gene.

3. The method according to claim 1, wherein the helper plasmid further comprises an inducible promoter that regulates expression of the gene encoding the endonuclease.

4. The method according to claim 1, wherein the plurality of linear nucleic acid fragments consist of a first linear nucleic acid fragment to an $n^{th}$ linear genome-introduced nucleic acid fragment, wherein n is an integer of 2 or more, and the 3'-terminal side of an $m^{th}$ linear genome-introduced nucleic acid fragment, wherein m is an integer satisfying $1 \leq m \leq n-1$, comprises a sequence capable of being homologously recombined with the 5'-terminal side of an $m^{th}+1$ linear nucleic acid fragment.

5. A transformation method comprising:
   introducing into a host yeast:
   (a) one or a plurality of linear nucleic acid fragments each comprising a gene of interest to be introduced into a predetermined position on a genome of the host yeast, and
   (b) a helper plasmid for transformation comprising a first homologous recombination sequence and a second homologous recombination sequence for incorporation of the linear nucleic acid fragments, a first and a second endonuclease target sequence, a gene encoding an endonuclease that specifically cleaves double strands of the first and the second endonuclease target sequences, a replication origin, and an autonomously replicating sequence (ARS),
   thereby producing a transformed host yeast comprising the circular plasmid, wherein the circular plasmid comprises: (i) the gene of interest, (ii) the first homologous recombination sequence, (iii) the first endonuclease target sequence upstream of the gene of interest, (iv) the second homologous recombination sequence, (v) second endonuclease target sequence downstream of the gene of interest, and (vi) the gene encoding the endonuclease;
   culturing the transformed host yeast comprising the circular plasmid under a condition to express the gene encoding the endonuclease, such that the circular plasmid is cleaved at the first and the second endonuclease target sequences by the endonuclease to produce a cleavage fragment comprising (i) the gene of interest, (ii) the first homologous recombination sequence upstream of the gene of interest, and (iii) the second homologous recombination sequence downstream of the gene of interest; such that homologous recombination to introduce the gene of interest into the genome of the transformed host yeast takes place at the first and the second homologous recombination sequences of the cleavage fragment,
   wherein the transformed host yeast expresses the gene of interest.

6. The transformation method according to claim 5, wherein the gene encoding the endonuclease is a homing endonuclease gene.

7. The transformation method according to claim 5, wherein the helper plasmid further comprises an inducible promoter that regulates expression of the gene encoding the endonuclease.

8. The transformation method according to claim 5, wherein the plurality of linear nucleic acid fragments consist of a first linear nucleic acid fragment to an $n^{th}$ linear genome-introduced nucleic acid fragment, wherein n is an integer of 2 or more, and the 3'-terminal side of an $m^{th}$ linear genome-introduced nucleic acid fragment, wherein m is an integer satisfying $1 \leq m \leq n-1$, comprises a sequence capable of being homologously recombined with the 5'-terminal side of an $m^{th}+1$ linear nucleic acid fragment.

* * * * *